(12) United States Patent
Chang et al.

(10) Patent No.: US 10,329,328 B2
(45) Date of Patent: Jun. 25, 2019

(54) HPV-RELATED FUSION PROTEIN AND APPLICATIONS THEREOF

(71) Applicant: ATTOGEN BIOMEDICAL (SUZHOU) INC. LTD., Suzhou, Jiangsu (CN)

(72) Inventors: Xiaojia Chang, Jiangsu (CN); Chenglong Shi, Jiangsu (CN); Lijun Shi, Jiangsu (CN); Jiecheng Zhang, Jiangsu (CN)

(73) Assignee: ATTOGEN BIOMEDICAL (SUZHOU) INC. LTD., Suzhou, Jiangsu (CN)

( * ) Notice: Subject to any disclaimer, the term of this patent is extended or adjusted under 35 U.S.C. 154(b) by 0 days.

(21) Appl. No.: 15/541,308

(22) PCT Filed: Dec. 28, 2015

(86) PCT No.: PCT/CN2015/099253
§ 371 (c)(1),
(2) Date: Jun. 30, 2017

(87) PCT Pub. No.: WO2016/107525
PCT Pub. Date: Jul. 7, 2016

(65) Prior Publication Data
US 2017/0349633 A1 Dec. 7, 2017

(30) Foreign Application Priority Data

Dec. 31, 2014 (CN) .......................... 2014 1 0851571

(51) Int. Cl.
| | | |
|---|---|---|
| *C07K 14/005* | (2006.01) | |
| *C07K 14/025* | (2006.01) | |
| *C07K 14/35* | (2006.01) | |
| *A61K 39/12* | (2006.01) | |
| *A61K 39/295* | (2006.01) | |
| *C12N 7/00* | (2006.01) | |
| *C12N 15/62* | (2006.01) | |
| *C12N 15/63* | (2006.01) | |
| *C07K 19/00* | (2006.01) | |
| *G01N 33/68* | (2006.01) | |
| *A61K 39/385* | (2006.01) | |
| *A61K 39/00* | (2006.01) | |

(52) U.S. Cl.
CPC ............ *C07K 14/005* (2013.01); *A61K 39/12* (2013.01); *A61K 39/295* (2013.01); *A61K 39/385* (2013.01); *C07K 14/025* (2013.01); *C07K 14/35* (2013.01); *C07K 19/00* (2013.01); *C12N 7/00* (2013.01); *C12N 15/62* (2013.01); *C12N 15/63* (2013.01); *G01N 33/68* (2013.01); *A61K 2039/572* (2013.01); *A61K 2039/575* (2013.01); *A61K 2039/6068* (2013.01); *C07K 2319/40* (2013.01); *C12N 2710/20022* (2013.01); *C12N 2710/20034* (2013.01); *C12N 2710/20071* (2013.01)

(58) Field of Classification Search
None
See application file for complete search history.

(56) References Cited

FOREIGN PATENT DOCUMENTS

| | | |
|---|---|---|
| CN | 1850863 | 10/2006 |
| CN | 101885778 | 11/2010 |
| CN | 102099053 | 6/2011 |
| CN | 103772508 | 5/2014 |
| CN | 103890177 | 6/2014 |
| EP | 3095798 | 11/2016 |
| WO | 2001/012216 | 2/2001 |

OTHER PUBLICATIONS

International search report for international application No. PCT/CN2015/099253, dated Mar. 25, 2016 (10 pages, including English translation).
Extended European Search Report, issued in the corresponding European patent application No. 15875201.4, dated Jun. 6, 2018, 14 pages.
K. Van Doorslaer et al., "Serological response to an HPV16 E7 based therapeutic vaccine in women with high-grade cervical dysplasia", Gynecologic Oncology, Academic Press, vol. 116, No. 2, pp. 208-212, 2010.
Chu et al., "Immunotherapy of a human papillomavirus (HPV) type 16 E7-expressing tumour by administration of fusion protein comprising *Mycobacterium bovis* bacille Calmette-Guérin (BCG) hsp65 and HPV16 E7", Clinical and Experimental Immunology, vol. 121, pp. 216-225, Aug. 2000.
Karanam et al., "Vaccination with HPV16 L2E6E7 fusion protein in GPI-0100 adjuvant elicits protective humoral and cell-mediated immunity", Vaccine, Elsevier, vol. 27, No. 7, pp. 1040-1049, 2009 and available at: https://www.sciencedirect.com/science/article/pii/S0264410X08016782?via%3Dihub.
Gambhira et al., "Vaccination of Healthy Volunteers with Human Papillomavirus Type 16 L2E7E6 Fusion Protein Induces Serum Antibody that Neutralizes across *Papillomavirus* Species", Cancer Research, vol. 66, No. 23, pp. 11120-11124, Dec. 1, 2006 and available at: http://cancerres.aacrjournals.org/content/66/23/11120.
Gottschalk et al., "Monocytes and the 38kDa-antigen of *Mycobacterium tuberculosis* modulate natural killer cell activity and their cytolysis directed against ovarian cancer cell lines", BMC Cancer, vol. 12, No. 1, pp. 1-11, 2012 and available at: https://bmccancer.biomedcentral.com/articles/10.1186/1471-2407-12-451.

*Primary Examiner* — Nicole Kinsey White
(74) *Attorney, Agent, or Firm* — Hamre, Schumann, Mueller & Larson, P.C.

(57) ABSTRACT

A fusion protein has a first antigen element, a second antigen element, and optionally a tag sequence and/or a signal peptide sequence. The first antigen element includes a polypeptide derived from the Mycobacterium tuberculosis Psts-1 protein. The second antigen element includes a polypeptide derived from a protein encoded by a HPV gene. The fusion protein can induce humoral immunity and cellular immunity to a high-risk HPV cancer protein and has anti-cancer activity in vivo.

16 Claims, 6 Drawing Sheets
Specification includes a Sequence Listing.

HPV-RELATED FUSION PROTEIN AND APPLICATIONS THEREOF

TECHNICAL FIELD

The present invention relates to field of the biology and medical, and in particular, relates to a construction method for recombinant vaccine having anti-cervical cancer cell activity and application thereof.

BACKGROUND ART

Human papilloma virus (HPV) is a small, non-enveloped virus that infects human epidermis and mucosal cells. At present, more than 100 kinds of HPV subtypes have been found. According to the pathogenicity, HPV is divided into low-risk type and high-risk type. The continuous infection of high-risk HPVs is closely related to the pathogenesis of some malignancies. Clinical trials, molecular biology studies and etiology studies have been shown that HPV infection is a major factor in the pathogenesis of cervical cancer (zur Hausen H. Papillomaviruses and cancer: from basic studies to Clinical application. Nat Rev Cancer 2002; 2: 342-50). A large number of epidemiological studies have been shown that HPV can be detected in 97% of cervical cancer, and HPV16 and HPV18 subtypes are highly correlated with the occurrence of cervical cancer. In addition to cervical cancer, HPV is also highly related to the occurrence of other cancers, such as oral cancer, esophageal cancer, head and neck cancer, rectum, anal cancer, lung cancer, and breast cancer. Therefore, the development of HPV genetic engineering vaccine is one of the important means for the prevention and treatment of cervical cancer and some other malignant tumors associated with HPV infection.

HPV vaccine can be divided into two categories of preventive vaccines and therapeutic vaccines. After the HPV infection, the body will produce neutralizing antibodies for HPV capsid protein L1 and L2 which can effectively protect the host from infection. Thus, preventive HPV vaccines are generally composed of viral capsid protein L1 or L1-L2 and can be self-assembled into hollow virus-like particles (VLPs) free of viral DNA in cells (Kirnbauer R, Taub J, Greenstone H, et al. Efficient self-assembly of human papillomavirus type 16 L1 and L1-L2 into virus like particles. J Virol [J]. 1993,67: 6929-36.). VLPs have the same antigenic epitope as the intact virus, and in a way, which can replace the natural virus to stimulate the body's $CD4^+$ lymphocyte-mediated humoral immune response and induce the production of a protective antibody against natural viruses, and can effectively protect the host from virus infection (Schiller J, Lowy D. Papillomavirus-like particle vaccines . JNatl Cancer Inst Monogr 2001; (28): 50-4).

The two existing preventive vaccines which are Merck's tetravalent vaccine of Gardasil and GlaxoSmithKline's bivalent vaccine of Cervarix, can effectively prevent the occurrence of cervical cancer by reducing the HPV infection ratio, but these vaccines can not treat HPV infection, nor can they treat HPV-associated malignant diseases (Trimble CL, Frazer IH. Development of therapeutic HPV vaccines. Lancet Oncol 2009; 10: 975-80). After HPV infection, viral DNA can be integrated into the human genome, and expressoncogenic proteins in the host cell. E6 and E7 proteins are generally overexpressed in cervical epithelial cells of the patients with high-grade cervical lesions and the cancer, leading to over-proliferation and malignant transformation of infected cells. As the virus oncogenic proteins E6 and E7 can be continuously expressed in the host tumor cells, and therefore the antigen target of immunotherapy for the HPV infection-related diseases can be provided. Thus, the therapeutic vaccine mainly uses HPV early proteins E6 and E7 as the target protein. For the treatment after HPV infection, the tumor residual lesions, cervical atypical hyperplasia (CIN) caused by HPV infection can be removed, the transition of low-risk lesions to high-risk type and cancer can be blocked (Nonn M, Schinz M, Zumbach K , Pawlita M, Schneider A, Dürst M, Kaufmann AM. Dendritic cell-based tumor vaccine for cervical cancer I: in vitro stimulation with recombinant protein-pulsed dendritic cells induces specific T cells to HPV16 E7 or HPV18 E7. J Cancer Res Clin Oncol. 2003; 129 (9): 511-20.).

HPV therapeutic vaccines can be divided into five categories: vector vaccines, peptide vaccines, protein vaccines, gene vaccines and cell vaccines. Protein vaccines can be divided into fusion protein vaccines and chimeric vaccines. Because a lesion may be caused by multiple types of HPV infection, the development of the preventive and/or therapeutic vaccines for variety types of HPV virus is a major challenge in HPV vaccine research, and possessing an important application value and future.

SUMMARY OF THE INVENTION

The object of the present invention is to provide a construction method for a recombinant vaccine having anti-cervical cancer cell activity and an application thereof.

In the first aspect of the invention, it provides a fusion protein comprising a first antigen element, a second antigen element, and optionally a tag sequence and/or a signal peptide sequence, wherein the first antigen element comprises a polypeptide derived from the Mycobacterium tuberculosis Psts-1 protein; and the second antigen element comprises a polypeptide derived from a protein encoded by a HPV gene.

In one preferred embodiment, the protein encoded by a HPV gene includes, but is not limited to, HPV L1 protein, HPV L2 protein, HPV E6 protein, HPV E7 protein.

In one preferred embodiment, the HPV includes, but is not limited to, HPV16, HPV18, HPV31, HPV33, HPV35, HPV39, HPV45, HPV51, HPV52, HPV56, HPV58, HPV59, HPV68.

In one preferred embodiment, the second antigen element is selected from one or more of the following groups:

an antigen element A, wherein the antigen element A is a polypeptide derived from HPV16 L2 protein;

an antigen element B, wherein the antigen element B is a polypeptide derived from HPV16 E6 protein;

an antigen element C, wherein the antigen element C is a polypeptide derived from HPV16 E7 protein; and an antigen element D, wherein the antigen element D is a polypeptide derived from the HPV18 E7 protein.

In one preferred embodiment, the length of the first antigen element is 15 to 30 amino acids, preferably 19 amino acids.

In one preferred embodiment, the length of the antigen element A is 10 to 30 amino acids, preferably 20 amino acids.

In one preferred embodiment, the length of the antigen element B is 5 to 20 amino acids, preferably 10 amino acids.

In one preferred embodiment, the length of the antigen element C is 40 to 60 amino acids, preferably 55 amino acids.

In one preferred embodiment, the length of the antigen element D is 50 to 100 amino acids, preferably 70 amino acids.

In one preferred embodiment, the antigen element comprises: an antigen element A, an antigen element B, an antigen element C, and an antigen element D.

In one preferred embodiment, the amino acid sequence of the Mycobacterium tuberculosis Psts-1 protein is shown in SEQ ID NO: 1.

In one preferred embodiment, the amino acid sequence of the HPV16 L2 protein is shown in SEQ ID NO.: 2.

In one preferred embodiment, the amino acid sequence of the HPV16 E6 protein is shown in SEQ ID NO: 3.

In one preferred embodiment, the amino acid sequence of the HPV16 E7 protein is shown in SEQ ID NO: 4.

In one preferred embodiment, the amino acid sequence of the HPV18 E7 protein is shown in SEQ ID NO: 5.

In one preferred embodiment, the first antigen element comprises amino acids 326-344 of the Mycobacterium tuberculosis Psts-1 protein.

In one preferred embodiment, the antigen element A comprises amino acids 17-36 of the HPV16 L2 protein.

In one preferred embodiment, the antigen element B comprises amino acids 29-38 of the HPV16 E6 protein.

In one preferred embodiment, the antigen element C comprises amino acids 36-90 of the HPV16 E7 protein.

In one preferred embodiment, the antigen element D comprises amino acids 31-100 of the HPV18 E7 protein.

In one preferred embodiment, the tag sequence is selected from: His tag, MBP tag.

In one preferred embodiment, the fusion protein has the following properties:

a) stimulating the body to produce humoral immune response against HPV;

b) stimulating the body to produce a cellular immune response against HPV;

c) inducing T lymphocyte proliferation;

d) inducing HPV-specific CTL responses.

In one preferred embodiment, the fusion protein has the structure of formula I:

M-C-A-D-B-T    (I), wherein,

M is the first antigen element;

A, B, C and D are the antigen element A, the antigen element B, the antigen element C, the antigen element D respectively, T is an optional tag sequence and/or a signal peptide sequence;

"-" means a peptide bond or a peptide linker linking the above-mentioned each elements.

In one preferred embodiment, the fusion protein is selected from the group consisting of:

(A) a polypeptide having an amino acid sequence as shown in SEQ ID NO: 11 or 14;

(B) a polypeptide having ≥80% (preferably ≥90%; more preferably ≥95%; most preferably ≥97%) identity with the amino acid sequence shown in SEQ ID NO: 11 or 14 and retaining the properties;

(C) a derivative polypeptide, which isformed from the amino acid sequence as shown in SEQ ID NO: 11 or SEQ ID NO: 14 by replacement, deletion, or addition of 1 to 5 amino acid residues, and retains the properties.

In the second aspect of the invention, it provides a polynucleotide encoding the fusion protein according to the first aspect of the invention.

In one preferred embodiment, the polynucleotide is DNA and/or RNA.

In one preferred embodiment, the RNA includes, but is not limited to, an mRNA sequence, an anti-sense RNA sequence, and a small interference RNA sequence.

In one preferred embodiment, the polynucleotide is selected from the group consisting of:

(a) a polynucleotide encoding a polypeptide as shown in SEQ ID NO.: 11 or 14;

(b) a polynucleotide having the sequence as shown in SEQ ID NO.: 12 or 13;

(c) a polynucleotide having ≥95% (preferably ≥98%) identity with the sequence shown in (b);

(d) a polynucleotide complementary to the polynucleotide described in any one of (a) to (c).

In one preferred embodiment, the polynucleotide sequence is shown in SEQ ID NO: 12 or 13.

In the third aspect of the invention, it provides a vector containing the polynucleotide according to the second aspect of the invention.

In one preferred embodiment, the vector has a backbone of pET-28a plasmid.

In the fourth aspect of the invention, it provides a host cell which expresses the fusion protein of the first aspect of the invention; and/or has the polynucleotide according to the second aspect of the invention integrated in the genome thereof, and/or contains the vector according to the third aspect of the invention.

In one preferred embodiment, the host cell is a prokaryotic or eukaryotic cell (such as a yeast cell).

In one preferred embodiment, the host cell comprises an *Escherichia coli*, a Yeast, a drosophila S2 cell, a CHO cell, a HEK293 cell, a DC cell and so on.

In one preferred embodiment, the host cell is an *E. coli* cell, preferably an *E. coli* BL21 strain.

In the fifth aspect of the invention, it provides a method for preparing a fusion protein, which comprises the following steps:

incubating the host cell according to the fourth aspect of the invention under conditions suitable for expression, thereby expressing the fusion protein according to the first aspect of the invention; and isolating the fusion protein.

In one preferred embodiment, the host cell is a prokaryotic or an eukaryotic cell. Preferably, the host cell is an *E. coli* cell. More preferably, the *E. coli* cell is an *E. coli* BL21 strain.

In the sixth aspect of the invention, it provides a pharmaceutical composition which comprises the fusion protein according to the first aspect of the invention, the polynucleotide according to the second aspect of the invention, or the vector according to the third aspect of the invention, and a pharmaceutically acceptable carrier and/or excipient.

In one preferred embodiment, the pharmaceutical composition comprises vaccine composition.

In the seventh aspect of the invention, it provides a vaccine composition which comprises the fusion protein according to the first aspect of the invention, the polynucleotide according to the second aspect of the invention, or the vector according to the third aspect of the invention, and an immunologically acceptable carrier and/or excipient.

In one preferred embodiment, the vaccine composition further comprises an adjuvant.

In one preferred embodiment, the adjuvant comprises alumina, Poly(I:C), saponin, quil A, muramyl dipeptide, mineral oil or vegetable oil, vesicle-based adjuvant, nonionic block copolymer or DEAE dextran, PEG (polyethylene glycol), cytokine (including IL-1, IL-2, IFN-γ, GM-CSF, IL-6, IL-12, and CpG).

In the eighth aspect of the invention, it provides a use of the fusion protein according to the first aspect of the invention, for preparing a medicament or a reagent for:

(1) treating or preventing HPV infection; and/or
(2) treating or preventing HPV infection-related diseases; and/or
(3) inducing an immune response against HPV; and/or
(4) detecting anti-HPV antibodies in serum.

In one preferred embodiment, the HPV infection-related diseases include, but are not limited to, gastric cancer, liver cancer, leukemia, kidney cancer, lung cancer, small intestine carcinoma, bone cancer, prostate cancer, colorectal cancer, breast cancer, carcinoma of large intestine, prostate cancer, cervical cancer, adrenal tumors, esophageal cancer, head and neck cancer, rectal cancer, oral cancer, anal cancer or bladder cancer.

In one preferred embodiment, the viral subtypes of the HPV include HPV16, HPV18, HPV31, HPV33, HPV35, HPV39, HPV45, HPV51, HPV52, HPV56, HPV58, HPV59, HPV68.

In the ninth aspect of the invention, it provides a method for treating HPV infection or HPV-related diseases, comprising the steps of: administering the fusion protein according to the first aspect of the present invention, the polynucleotide (DNA, RNA, RNAi, anti-sense RNA) according to the third aspect of the present invention, the pharmaceutical composition according to the sixth aspect of the present invention, or the vaccine composition according to the seventh aspect of the present invention to a subject in need thereof.

In one preferred embodiment, the fusion protein is administered in the form of a monomer and/or a dimer.

In one preferred embodiment, the subject is human.

It should be understood that in the present invention, the technical features specifically described above and below (such as the Examples) can be combined with each other, thereby constituting a new or preferred technical solution, which needs not be specified one by one.

DETAILED DESCRIPTION OF INVENTION

Figure 1:
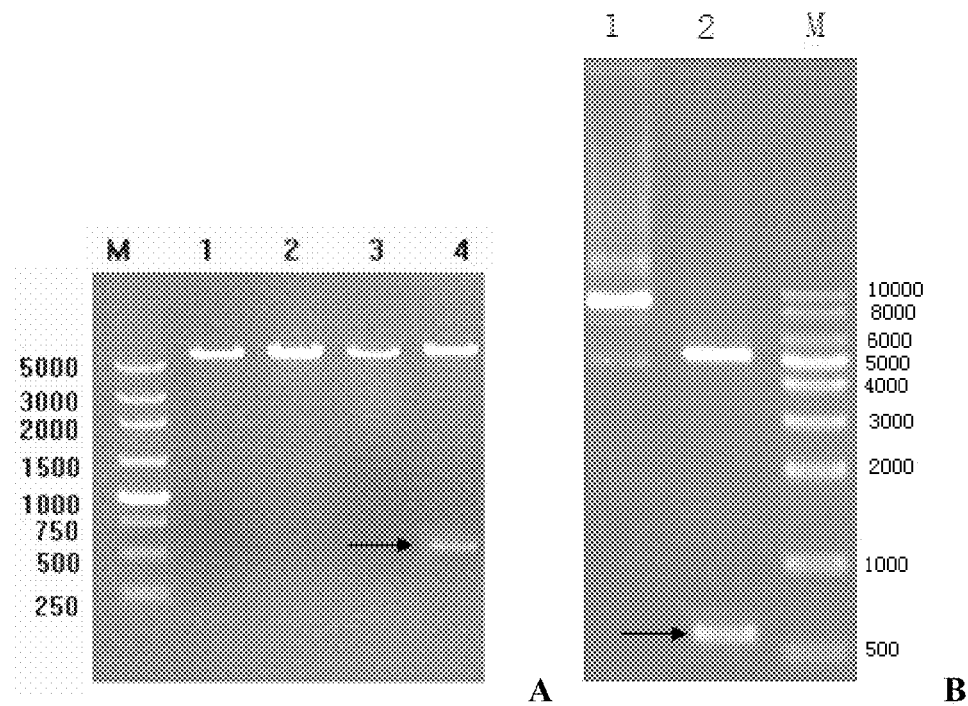
FIG. 1 shows the electrophoresis pattern of digested clonal vector. A is the identification result of four digested pET-VAC-Pro clones, and B is the identification result of digested pET-VAC clone.

Through extensive and intensive researches, the inventors of the present invention has obtained a fusion protein targeting HPV oncogenic proteins, and the experimental results show that the fusion protein can simultaneously induce against high-risk HPV to produce humoral immunity (antibody activity), cellular immunity (T-cell activity), and in vivo anti-tumor activity and which can be used for the development of prophylactic and therapeutic vaccines for HPV infection-related cancers, such as cervical cancer.

Active Polypeptide

The present invention provides an HPV-related fusion protein comprising a polypeptide derived from the Mycobacterium tuberculosis (MT) Psts-1 protein; a polypeptide derived from the HPV16 L2 protein; a polypeptide derived from the HPV16 E6 protein; a polypeptide derived from the HPV16 E7 protein; a polypeptide derived from the HPV18 E7 protein, and optionally a tag sequence and/or a signal peptide sequence.

As used herein, the term "derived from" includes:

(A) truncating a shorter polypeptide fragment from a longer polypeptide;
(B) polypeptide I can be defined as a polypeptide derived from polypeptide II, when polypeptide I have ≥80% (preferably ≥90%, more preferably ≥95%, most preferably ≥98%) identity compared with a fragment of polypeptide II.

In a preferred embodiment of the present invention, the GenBank accession number of the Mycobacterium tuberculosis Psts-1 protein is P9WGU0.1; the GenBank accession number of the HPV16-L2 protein is AHK23261.1; the GenBank accession number of the HPV16-E6 protein is ABK32509.1; the GenBank accession number of HPV16-E7 protein is AHK23257.1; the GenBank accession number of HPV18-E7 protein is AAP20595.1.

In a preferred embodiment of the present invention, the amino acid sequence of the Mycobacterium tuberculosis Psts-1 protein is as follows:

```
                                        (SEQ ID NO.: 1)
MKIRLHTLLAVLTAAPLLLAAAGCGSKPPSGSPETGAGAGTVATTPASSPV

TLAETGSTLLYPLFNLWGPAFHERYPNVTITAQGTGSGAGIAQAAAGTVNI

GASDAYLSEGDMAAHKGLMNIALAISAQQVNYNLPGVSEHLKLNGKVLAAM

YQGTIKTWDDPQIAALNPGVNLPGTAVVPLHRSDGSGDTFLFTQYLSKQDP
```

-continued

EGWGKSPGFGTTVDFPAVPGALGENGNGGMVTGCAETPGCVAYIGISFLDQ

ASQRGLGEAQLGNSSGNFLLPDAQSIQAAAAGFASKTPANQAISMIDGPAP

DGYPIINYEYAIVNNRQKDAATAQTLQAFLHWAITDGNKASFLDQVHFQPL

PPAVVKLSDALIATISS.

In a preferred embodiment of the invention, the amino acid sequence of the
HPV16-L2 protein is as follows:

(SEQ ID NO.: 2)
MRHKRSAKRTKRASATQLYKTCKQAGTCPPDIIPKVEGKTIADQILQYGSM

GVFFGGLGIGTGSGTGGRTGYIPLGTRPPTATDTLAPVRPPLTVDPVGPSD

PSIVSLVEETSFIDAGAPTSVPSIPPDVSGFSITTSTDTTPAILDINNTVT

TVTTHNNPTFTDPSVLQPPTPAETGGHFTLSSSTISTHNYEEIPMDTFIVS

TNPNTVTSSTPIPGSRPVARLGLYSRTTQQVKVVDPAFVTTPTKLITYDNP

AYEGIDVDNTLYFPNNDNSINIAPDPDFLDIVALHRPALTSRRTGIRYSRI

GNKQTLRTRSGKSIGAKVHYYYDFSTIDPAEEIELQTITPSTYTTTSHAAS

PTSINNGLYDIYADDFITDTFTTPVPSVPSTSLSGYIPANTTIPFGGAYNI

PLVSGPDIPINITDQAPSLLPIVPGSPQYTIIADAGDFYLHPSYYMLRKRR

KRLPYFFSDVSLAA.

In a preferred embodiment of the invention, the amino acid sequence of the
HPV16-E6 protein is as follows:

(SEQ ID NO.: 3)
MHQKRTAMFQDPQERPRKLPHLCTELQTTIHDIILECVYCKQQLLRREVYD

FAFRDLCIVYRDGNPYAVCDKCLKFYSKISEYRYYCYSVYGTTLEQQYNKP

LCDLLIRCINCQKPLCPEEKQRHLDKKQRFHNIRGRWTGRCMSCCRSSRTR

RETLL.

In a preferred embodiment of the invention, the amino acid sequence of the HPV16-E7 protein is as follows:

(SEQ ID NO.: 4)
MHGDTPTLHEYMLDLQPETTDLYCYEQLNDSSEEEDEIDGPAGQAEPDRAH

YNIVTFCCKCDSTLRLCVQSTHVDIRTLEDLLMGTLGIVCPICSQKP.

In a preferred embodiment of the invention, the amino acid sequence of the
HPV18-E7 protein is as follows:

(SEQ ID NO.: 5)
MHGPKATLQDIVLHLEPQNEIPVDLLCHEQLSDSEEENDEIDGVNHQHLPA

RRAEPQRHTMLCMCCKCEARIELVVESSADDLRAFQQLFLNTLSFVCPW.

In a preferred embodiment of the invention, the fusion protein comprises successively tandem amino acids 350 to 368 of Mycobacterium tuberculosis (MT) Psts-1 protein (SEQ ID NO.: 1), amino acids 36 to 90 of HPV16 E7 protein (SEQ ID NO.: 4), amino acids 17 to 36 of the HPV16 L2 protein (SEQ ID NO.: 2), amino acids 31 to 100 of the HPV18 E7 protein (SEQ ID NO.: 5), amino acids 29 to 38 of the HPV16 E6 protein (SEQ ID NO.: 3), and His tag.

In a preferred embodiment of the invention, the amino acid sequence of the fusion protein comprises
DQVHFQPLPPAVVKLSDAL(SEQ ID NO.:6,derived from Mycobacterium tuberculosis Psts-1 protein).

In a preferred embodiment of the invention, the amino acid sequence of the fusion protein comprises
QLYKTCKQAGTCPPDIIPKV(SEQ ID NO.:7,derived from HPV16 L2 protein).

In a preferred embodiment of the invention, the amino acid sequence of the fusion protein comprises
TIHDIILECV(SEQ ID NO.:8,derived from HPV16 E6 protein).

In a preferred embodiment of the invention, the amino acid sequence of the fusion protein comprises
DEIDGPAGQAEPDRAHYNIVTFCCKCDSTLRL-CVQSTHVDIRTLEDLLM GTLGIV (SEQ ID NO.:9,derived from HPV16 E7 protein).

In a preferred embodiment of the invention, the amino acid sequence of the fusion protein comprises
LSDSEEENDEIDGVNHQHLPARRAEPQRHTMLCM-CCKCEARIELVVESS ADDLRAFQQLFLNTLSFVCPW (SEQ ID NO.:10,derived from HPV18 E7 protein).

In a preferred embodiment of the invention, the amino acid sequence of the fusion protein comprises (SEQ ID NO.: 11)
DQVHFQPLPPAVVKLSDALDEIDGPAGQAEPDRAHYNIVTFCCKCDSTLRL

CVQSTHVDIRTLEDLLMGTLGIVQLYKTCKQAGTCPPDIIPKVLSDSEEEN

DEIDGVNHQHLPARRAEPQRHTMLCMCCKCEARIELVVESSADDLRAFQQL

FLNTLSFVCPWTIHDIILECV

In a preferred embodiment of the present invention, the method of constructing said HPV-related fusion protein comprises, providing a coding sequence of a fusion protein composed of MTPsts-1 protein fragment, an HPV16 E6 protein fragment, an HPV16 E7 protein fragment, an HPV16 L2 protein fragment and HPV18 E7 protein fragment for enhancing an immune response. The gene sequence is cloned into an *E. coli* expression vector by molecular bioengineering method and expressed in *E. coli*.

In a preferred embodiment of the invention, the nucleic acid sequence encoding the fusion protein comprises (SEQ ID NO.: 12)
atgagcgaccaggttcacttccagccgctgccgccggctgttgttaaactg tctgacgctctggatgaaatagatggtccagctggacaagcagaaccggac agagcccattacaatattgtaaccttttgttgcaagtgtgactctacgctt cggttgtgcgtacaaagcacacacgtagacattcgtactttggaagacctg ttaatgggcacactaggaattgtgcaactttataaaacatgcaaacaggca ggtacatgtccacctgacattatacctaaggttttaagcgactcagaggaa gaaaacgatgaaatagatggagttaatcatcaacatttaccagcccgacga gccgaaccacaacgtcacacaatgttgtgtatgtgttgtaagtgtgaagcc agaattgagctagtagtagaaagctcagcagacgaccttcgagcattccag cagctgtttctgaacaccctgtcctttgtgtgtccgtggactatacatgat ataatattagaatgtgtgcatcatcatcatcatcac In a preferred embodiment of the invention, the nucleic acid sequence encoding the fusion protein comprises (SEQ ID NO.: 13, gene sequence optimized according to E. coli codon)
atgggtgatcaggtgcattttcaaccgctgccgccggctgtggtcaaactg tccgacgctctggatgaaatcgacggtccggctggtcaggcagaaccggat cgcgctcattacaacatcgtgaccttctgctgtaaatgcgattcaacgctg cgtctgtgtgtccagtcgacccacgtggatattcgcacgctggaagacctg ctgatgggcaccctgggtatcgttcagctgtacaaaacctgcaaacaagca ggcacgtgtccgccggatattatcccgaaagttctgagtgactccgaagaa gaaaacgatgaaattgacggtgtcaatcatcagcacctgccggcacgtcgc gcagaaccgcaacgtcataccatgctgtgcatgtgctgtaaatgtgaagcc cgcatcgaactggtggttgaaagctctgcggatgacctgcgtgcctttcag caactgttcctgaatacgctgtctttcgtgtgcccgtggacgattcacgac atcatcctggaatgcgttcatcatcatcaccatcac.

In a preferred embodiment of the present invention, the expression vector used in the present invention is pET-VAC, and the recombinant protein expressed by this vector is His-Vac and its amino acid sequence is (SEQ ID NO.: 14)
DQVHFQPLPPAVVKLSDALDEIDGPAGQAEPDRAHYNIVTFCCKCDSTLRL

CVQSTHVDIRTLEDLLMGTLGIVQLYKTCKQAGTCPPDIIPKVLSDSEEEN

DEIDGVNHQHLPARRAEPQRHTMLCMCCKCEARIELVVESSADDLRAFQQL

FLNTLSFVCPWTIHDIILECVHHHHHH.

The fusion protein of the present invention has the following properties:
a) stimulating the body to produce humoral immune response against HPV;
b) stimulating the body to produce a cellular immune response against HPV;
c) inducing T lymphocyte proliferation;
d) inducing HPV-specific CTL responses.

As used herein, the term "fusion protein" further comprises variants of SEQ ID NO: 11 or 14 exhibiting above activity. These variations include, but are not limited to, deletions, insertions and/or substitutions of 1-3 (typically 1-2, more preferably 1) amino acids, and additions or deletions of one or more (typically less than 3, preferably less than 2, more preferably less than 1) amino acids at C-terminus and/or N-terminus. For example, a protein's functions are usually unchanged when an amino acid is substituted by another amino acid with similar or analogous properties in the art. For another example, generally, the structure and function of protein won't be changed by the addition or deletion of one or several amino acids at C-terminus and/or N-terminus. In addition, the term also encompasses the polypeptides of the present invention in monomeric and multimeric forms. The term also includes linear and non-linear polypeptides (such as cyclic peptides).

The present invention further includes the active fragments, derivatives and analogs of the fusion protein. As used herein, the terms "fragments", "derivatives" and "analogs" refer to the polypeptides substantially maintaining the function or activity of the fusion protein of the present invention. The polypeptide fragments, derivatives or analogs of the present invention may be (i) a polypeptide with one or more conservative or non-conservative amino acid residues (preferably the conservative amino acid residues) being substituted, or (ii) a polypeptide having substituted group(s) in one or more amino acid residues, or (iii) a polypeptide formed by fusion of the antigen peptide with another compound (such as the compound that prolongs the half life of the polypeptide, such as polyethylene glycol), or (iv) a polypeptide formed with additional amino acid sequence fused to said polypeptide sequence, such as fusion proteins formed by fusion with leader sequence, secretion sequence or tag sequence, such as 6His. According to the teachings herein, these fragments, derivatives and analogs are within the scope commonly known by the skilled person.

In the present invention, a preferred active derivative refers to the polypeptides formed by replacing at most 3, preferably at most 2, more preferably at most 1 amino acid with the amino acid having similar or analogous property, compared with the amino acid sequence of formula Ia or formula Ib. These conservative variant polypeptides are preferably formed by carrying out the amino acid replacement according to Table A.

TABLE A

| Initial residue | Representative substitution | Preferred substitution |
| --- | --- | --- |
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro; Ala | Ala |
| His (H) | Asn; Gln; Lys; Arg | Arg |
| Ile (I) | Leu; Val; Met; Ala; Phe | Leu |
| Leu (L) | Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Leu |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala | Leu |

The present invention also provides analogues of the fusion protein of the present invention. These analogues can differ from the polypeptide of SEQ ID NO.11 in amino acid sequence or in modifications that do not affect the sequence, or both. Also included are analogues which include residues other than those naturally occurring L-amino acids (e.g., D-amino acids) or non-naturally occurring or synthetic amino acids (e.g., β- or γ-amino acids). It is understood that the polypeptides of the present invention are not limited to the representative polypeptides listed herein above.

Modifications (which do not normally alter the primary sequence) include in vivo or in vitro chemical derivation of polypeptides, e.g., acelylation, or carboxylation. Also included is modification of glycosylation, e.g., the polypeptides produced through glycosylation modification during its synthesis and processing or in the further processing steps. These modifications can be conducted by exposing the polypeptide to glycosylation enzymes (e.g., mammalian glycosylation or deglycosylation enzymes). Also included are sequences that have phosphorylated amino acid residues, e.g., phosphotyrosine, phosphoserine, phosphothronine, as well as sequences that have been modified to improve their resistance to proteolytic degradation or to optimize solubility properties.

The polypeptides of the present invention (the fusion protein) can be used in a form of pharmaceutically or physiologically acceptable salts derived from acid or base. Such salts include, but are not limited to, the salts formed with the following acids: hydrochloric acid, hydrobromic acid, sulfuric acid, citric acid, tartaric acid, phosphoric acid, lactic acid, pyruvic acid, acetic acid, succinic acid, oxalic acid, fumaric acid, maleic acid, oxaloacetic acid, methane-sulfonic acid, ethyl-sulfonic acid, benzene sulfonic acid, or isethionic acid. Other salts include salts formed with alkali metals or alkaline earth metals (such as sodium, potassium, calcium or magnesium), and esters, carbamate or other conventional "prodrug" forms.

Encoding Sequences

The present invention further relates to a polynucleotide encoding the fusion protein of the present invention.

The polynucleotide of the present invention can be in a form of DNA or RNA. DNA can be the coding strand or the non-coding strand. The coding sequence encoding the mature polypeptide can be identical with that encoding the peptide shown in SEQ ID NO: 11, or can be a degenerate variant thereof. As used herein, in the present invention, "degenerate variant" refers to a nucleic acid sequence which encodes the protein having the amino acid sequence of SEQ ID NO:11, but is different from the corresponding coding sequence.

In a preferred embodiment of the invention, the sequence of the polynucleotide is shown in SEQ ID NO.: 12 or 13.

The full length of nucleotide sequence or fragment thereof of the present invention can be obtained via PCR amplification, recombinant method or artificial synthesis. Currently, the DNA sequence encoding the polypeptide (or fragment or derivative thereof) of the present invention can be prepared completely via chemical synthesis. Then the DNA sequence can be introduced into various existing DNA molecules (or such as vector) and cells known in the art.

The present invention also includes a vector containing the polynucleotide of the present invention, and a host cell produced by gene engineering of the vector or the coding sequence of the polypeptide of the present invention. The above polynucleotides, vectors or host cells may be isolated.

As used herein, the term "isolated" refers to that the substance is separated from its original environment (if it is a natural substance, the original environment is a natural environment). For example, the polynucleotides and polypeptides in the native state of the living cells are not isolated and purified, and the same polynucleotides or polypeptides are isolated and purified if they are separated from other substances present in the natural state.

The polynucleotides of the present invention may be in the form of DNA or RNA. DNA forms include cDNA, genomic DNA, or synthetic DNA. DNA can be single-stranded or double-stranded. DNA can be a coding or noncoding chain.

The present invention also relates to variants of the polynucleotides as described above, which encode fragments, analogs and derivatives of proteins having the same amino acid sequence as that in the present invention. Variants of such polynucleotides may be naturally occurring allelic variants or non-naturally occurring variants. Such nucleotide variants include substitutions of variants, deletions of variants, and insertions of variants. As is known in the art, an allelic variant is an alternative form of a polynucleotide, which may be a substitution, deletion or insertion of one or more nucleotides, but the function of the polypeptide encoded by the polynucleotide will not be substantially altered.

As used herein, the term "primer" refers to the generic terms for oligonucleotides that are capable of synthesizing a DNA strand that is complementary to a template under the action of DNA polymerase from itsstarting point. Primers can be the natural RNA, DNA, and can be any forms of natural nucleotides. Primers can even be non-natural nucleotides such as LNA or ZNA. The primer is "substantially" (or "essentially") complementary to a particular sequence on a chain on the template. Primers must be fully complementary to a strand on the template for extension, but the sequence of primers does not have to be completely complementary to the sequence of the template. For example, the 5' end of the primer which has a 3' end complementary to the template is added with a sequence that is not complementary to the template, and such primers are still substantially complementary to the template. As long as there are long enough primers to fully bind to the template, non-fully complementary primers can also be used to form primers—template complexes with the template for amplification.

A nucleotide full length sequence or fragment thereof of the polypeptide of the present invention can generally be obtained by a PCR amplification method, a recombinant method or an artificial synthetic method. For a PCR amplification method, primers can be designed according to the relevant nucleotide sequences disclosed in the present invention, particularly the open reading frame sequences, and the commercially available cDNA libraries or cDNA libraries prepared by the conventional methods known to the skilled in the art were used as a template, and amplified and the relevant sequences were obtained. When the sequence is longer, two or more PCR amplifications are usually needed, and then each of the amplified fragments are spliced together in the correct order.

Once the relevant sequence is obtained, the relevant sequence can be obtained in bulk using a recombination method. Usually cloned into a vector, then transferred into a cell, and then the relevant sequence is seperated and obtained from the proliferation of host cells by the conventional method.

In addition, the relevant sequence can also be synthesized using artificial synthesis methods, particularly when the fragment is shorter. In general, a very long fragment can be obtained by firstly synthesizing multiple small fragments and then ligating them.

The method of amplifying DNA/RNA using PCR technology is preferably used to obtain the gene of the present invention. Primers for PCR can be appropriately selected according to the sequence information of the present invention disclosed herein and can be synthesized by conventional methods. The amplified DNA/RNA fragments can be isolated and purified by conventional methods such as by gel electrophoresis. The present invention also relates to a vector containing the polynucleotide of the present invention, and a host cell produced by genetic engineering using a vector or a protein encoding sequence of the present invention, and a method for producing the polypeptide of the present invention by recombinant techniques.

With the conventional recombinant DNA technique, the polynucleotide sequence of the present invention can be used to express or produce the fusion protein of the present invention. Generally, the method comprises the following steps:

(1) transforming or transducing a suitable host cell with a polynucleotide or variant thereof encoding the polypeptide of the present invention or a recombinant expression vector containing said polynucleotide;

(2) culturing the host cell in a suitable culture medium;

(3) isolating and purifying the fusion protein from the culture medium or cell.

An expression vector containing an encoding DNA sequence of a enzyme and a suitable transcription/translation control signal of the present invention can be constructed by the methods well known to the skilled in the art. These methods include recombinant DNA technology in vitro, DNA synthesis technology, recombination techniques in vivo. The DNA sequence described herein can be effectively linked to a suitable promoter in an expression vector to direct mRNA synthesis. The expression vector also includes a ribosome binding site for translation initiation and a transcription terminator.

In addition, the expression vector preferably comprises one or more selectable marker genes to provide the selection of phenotypic traits for the transformed host cells, such as dihydrofolate reductase for eukaryotic cell culture, neomycin resistance, and green fluorescent protein (GFP), or tetracycline or ampicillin resistance for *E. coli*.

A vector comprising an appropriate DNA sequence and a suitable promoter or a control sequence as described above can be used to transform an appropriate host cell to enable it to express the protein.

A host cell can be a prokaryotic cell, such as a bacterial cell; or a lower eukaryotic cell, such as a yeast cell; or a higher eukaryotic cell, such as mammalian cells. Representative examples are: bacterial cells such as *Escherichia coli*, *Bacillus subtilis* and *Streptomyces*; fungal cells such as *Pichia pastoris, Saccharomyces cerevisiae*; plant cells; insect cells of fruit flies S2 or Sf9; animal cells of CHO, NS0, COS7, or 293 cells and the like.

Transformation of host cells with recombinant DNA can be carried out using conventional techniques well known to the skilled in the art. When the host is a prokaryote such as *E. coli*, competent cells capable of absorbing DNA can be harvested after the exponential growth stage and treated with $CaCl_2$, the steps used are well known in the art. Another method is to use $MgCl_2$. If necessary, the transformation can also be carried out by means of electroporation. When the host is an eukaryote, the following DNA transfection methods are available: calcium phosphate coprecipitation, conventional mechanical methods such as microinjection, electroporation, liposome packaging, and the like.

The obtained transformants can be cultured by a conventional method to express a protein encoded by a gene of the present invention. According to the host cell used, the medium used in the culture may be selected from a variety of conventional media. And the host cell can be cultured under conditions suitable for the growth of the host cell. After the host cell grows to the appropriate cell density, the selected promoter is induced with a suitable method, such as temperature conversion or chemical induction, and the cells are incubated for a further period of time.

The protein in the above-mentioned method may be expressed in the cells, or expressed on the cell membrane, or secreted out of the cell. If desired, the protein can be isolated and purified according to the physical, chemical and other properties thereof by various isolation methods. These methods are well-known to those skilled in the art and include, but are not limited to, conventional renaturation treatment, treatment by protein precipitant (such as salt precipitation), centrifugation, cell lysis by osmosis, sonication, supercentrifugation, molecular sieve chromatography (gel chromatography), adsorption chromatography, ion exchange chromatography, high performance liquid chromatography (HPLC), and any other liquid chromatography, and combinations thereof.

Preparation Method

The fusion protein (polypeptide) of the present invention can be a recombinant or synthetic polypeptide. The polypeptide of the present invention can be a chemically synthesized or recombinant polypeptide. Accordingly, the polypeptide of the present invention can be artificially synthesized via a conventional method, or can be produced via a recombinant method.

A preferred method is the use of liquid phase synthesis techniques or solid phase synthesis technique, such as Boc solid phase process, Fmoc solid phase process, or combination thereof. By using the solid phase synthesis, a sample can rapidly be obtained, and one can select a suitable resin carrier and synthesis system according to the sequence feature of the target peptide. For example, the preferred solid phase carrier in Fmoc system can be, such as Wang resin linked to the C-terminal amino acid of the peptide, wherein the structure of the Wang resin is polystyrene, the arm between the resin and the amino acid is 4-alkoxy benzyl alcohol. The Wang resin is treated with 25% hexahydropyridine/dimethylfomamide for 20 minutes at room temperature to remove the Fmoc protective groups. Then the sequence is extended one by one from the C-terminus to the N-terminus according to the predetermined amino acid sequence. After synthesis, trifluoroacetic acid containing 4% p-methylphenol is used to cleave the proinsulin peptide from the resin and the protective groups are removed. The resin can be filtered off, and the crude peptide can be obtained via precipitation and seperation with ether. The solution of the resultant product is freeze-dried, gel-filtered, and purified by reverse phase HPLC to obtain the desired peptide. When utilizing the Boc system to perform the solid phase synthesis, preferably the resin is the PAM resin linked to the C-terminal amino acid of the peptide. The structure of the PAM resin is polystyrene, and the arm between the resin and the amino acid is 4-hydroxylmethyl phenylacetamide. In the Boc synthesis system, in the circle of deprotection, neutralization, and coupling, TFA/dichloromethane (DCM) is used to remove the protective group Boc, and diisopropylethylamine (DIEA)/ dichloromethane is used for neutralization. After completion of peptide chain condensation, hydrogen fluoride (HF) containing p-methylphenol (5-10%) is used to treat the resin for 1 hour at 0° C., then the peptide chain is cleaved from the resin and the protective groups are removed at the same time. 50-80% acetic acid (containing a small amount of mercaptoethanol) is used to extract the peptide. The solution is freeze-dried, and then further isolated and purified by molecular sieve Sephadex G10 or Tsk-40f. Then the desired peptide is obtained via high pressure liquid purification. Various coupling agents and coupling methods known in the peptide chemistry can be used to couple each amino acid residue. For example, dicyclohexylcarbodiimide (DCC), hydroxylbenzotriazole (HOBt) or 1,1,3,3-tetramethyluronium Hexafluorophosphate (HBTU) can be used for direct coupling. The purity and structure of the resultant short peptide can be verified by reverse phase HPLC and mass spectrometry.

In a preferred embodiment, the fusion protein of the present invention is prepared by solid phase method according to its sequence, and purified by high performance liquid chromatography, thereby obtaining freeze-dried powder of target peptide with high purity. The powder is stored at −20° C.

Another method is to produce the polypeptide of the present invention by a recombinant technique. By the conventional recombinant DNA technique, the polynucleotide of the present invention can be used to express or produce the fusion protein. Generally, the method comprises the following steps:

(1) Transforming or transducing a suitable host cell with a polynucleotide or variant thereof encoding the fusion protein of the present invention or a recombinant expression vector containing said polynucleotide;

(2) Culturing the host cell in a suitable culture medium;

(3) Isolating and purifying protein from the culture medium or cells.

The recombinant polypeptide may be expressed in the cells, or expressed on the cell membrane, or secreted out of the cell. If desired, the recombinant protein can be isolated and purified according to the physical, chemical and other properties thereof by various isolation methods. These methods are well-known to those skilled in the art and include, but are not limited to, conventional renaturation treatment, treatment by protein precipitant (such as salt precipitation), centrifugation, cell lysis by osmosis, sonication, supercentrifugation, molecular sieve chromatography (gel chromatography), adsorption chromatography, ion exchange chromatography, high performance liquid chromatography (HPLC), and any other liquid chromatography, and combinations thereof.

It is also contemplated to link multiple polypeptides of the present invention in series due to their short length. After recombinant expression, the expressed product of the multimeric form is obtained and enzyme-cleaved to form the desired small peptides.

Pharmaceutical Composition and Methods of Administration

The fusion protein of the present invention can be used as an immunogen to induce antibodies and lymphoid T cell activity against HPV or HPV positive cells in vivo, thereby achieving therapeutic effects. In addition, the antigenic peptide of the present invention has excellent specificity and immunological activity and can be used for preparing a vaccine for immunotherapy or prophylaxis.

In another aspect, the present invention further provides a pharmaceutical composition (including vaccine), comprising (a) a safe and effective amount of the polypeptide of the present invention or a pharmaceutically acceptable salt thereof (or the encoding sequence thereof); and (b) a pharmaceutically acceptable carrier or excipient. The amount of the polypeptide of the present invention generally is 10 μs to 100 mg per dose, preferably 100-1000 μs per dose.

For the purpose of the invention, the effective dose is about 0.01mg to 50 mg of the polypeptide of the present invention per kg body weight, preferably 0.05 mg to 10 mg of the polypeptide of the present invention per kg body weight administered to an individual. Further, the polypeptide of the present invention can be used alone, or in combination with other therapeutic agents (for example, formulated into the same pharmaceutical composition).

The pharmaceutical composition can further comprise a pharmaceutically acceptable carrier. The term "pharmaceutically acceptable carrier" refers to the carrier used in administering the therapeutic agents. The term refers to such drug carriers that themselves do not induce the occurrence of antibody deleterious to the subject receiving the composition, and do not produce excessive toxicity upon administration. These carriers are well known by the skilled person in the art. The detailed discussion about pharmaceutically acceptable excipients can be found in Remington's Pharmaceutical Sciences (Mack Pub. Co., N.J., 1991). Such carriers include, but are not limited to, saline, buffer solution, glucose, water, glycerin, ethanol, adjuvant or combinations thereof.

The pharmaceutically acceptable carrier in the therapeutic composition can comprise liquid, such as water, saline, glycerin, and ethanol. Moreover, these carriers can contain auxiliary substance(s), such as wetting agent or emulsifying agent, pH buffering substance, etc.

Typically, the therapeutic composition can be formulated into an injectable formulation, such as a liquid solution or suspension; or it may be in a solid form that is suitable to be formulated into a solution or suspension or liquid carrier before inj ection.

Once formulating the composition of the present invention, it can be administered via conventional routes which include, but are not limited to, administering intramuscularly, intravenously, subcutaneously, intracutaneously or topically. The subject to be prevented or treated may be an animal, especially a human.

When the pharmaceutical composition of the present invention is used in the actual treatment, the dosage form of the pharmaceutical composition can be varied according to the uses. Preferably, the dosage form may be injection.

The pharmaceutical composition can be formulated by mixing, diluting or dissolving according to the conventional methods. Besides, suitable medicine additives, such as excipients, disintegrating agents, adhesives, lubricants, diluting agents, buffering agents, isotonicities, preservatives, wetting agents, emulsifying agents, dispersing agents, stabilizing agents, and cosolvent, may occasionally be added. Formulation can be carried out in a conventional manner according to the dosage form.

The pharmaceutical composition of the present invention can further be administered in a form of slow release formulation. For example, the fusion protein or a salt thereof can be incorporated into a pill or microcapsule in which a slow release polymer is used as a carrier, and then the pill or microcapsule is implanted into the human tissue by operation. Examples of the slow release polymer include ethylene-ethylene acetate copolymer, polyhydroxymethylacrylate, polyacrylamide, polyvinylpyrrolidone, methyl cellulose, polymer of lactic acid, lactic acid-glycolic acid copolymer, etc., Preferable examples of the slow release polymer include the biodegradable polymers, such as polymer of lactic acid, and lactic acid-glycolic acid copolymer.

When the pharmaceutical composition of the present invention is used for prophylaxis or treatment, the dose of the fusion protein or a pharmaceutically acceptable salt thereof as an active ingredient, can be suitably determined according to the body weight, age, gender, symptom of each subject (patient) to be prevented or treated.

A vaccine (composition) according to the invention may either be prophylactic (i.e., to prevent disease, for example: prevention of cancer caused by HPV infection) or therapeutic (i.e., to treat disease after sickness, for example: cervical cancer or precancerous lesions).

Such vaccines comprise an immunizing antigen (including the recombinant protein of the invention), usually in combination with "pharmaceutically acceptable carriers," which include any carriers that themselves do not induce the production of antibodies harmful to the individuals receiving the composition. Suitable carriers are typically large, slowly metabolized macromolecules such as proteins, polysaccharides, polylactic acids, polyglycolic acids, amino acids polymers, amino acid copolymers, lipid agglutinates (such as oil droplets or liposomes), and so on. Such carriers are well known to those of ordinary skilled in the art. Additionally, these carriers may function as immunostimulating agents ("adjuvants"). Furthermore, the antigen may be conjugated to a bacterial toxoid, such as a toxoid of diphtheria, tetanus, cholera, H. pylori, or other pathogens. Preferably, the construct of the vaccine of the present invention is to use a polypeptide fragment of a Mycobacterium tuberculosis antigen.

Preferred adjuvants to enhance effectiveness of the vaccine composition include, but are not limited to: (1) aluminum salts (alum), such as aluminum hydroxide, aluminum phosphate, aluminum sulfate, etc; (2) oil-in-water emulsion formulations, such as (a) MF59 (see WO 90/14837), (b) SAF, and (c) RIBI™ adjuvant system (RAS), (Ribi Immunochem, Hamilton, Mont.); (3) saponin adjuvants; (4) Complete Freund's Adjuvant (CFA) and Incomplete Freund's Adjuvant (IFA); (5) cytokines, such as interleukins (e.g., IL-1, IL-2, IL-4, IL-5, IL-6, IL-7, IL-12, etc.), interferons (e.g., γ interferon), macrophage colony stimulating factor (M-CSF), tumor necrosis factor (TNF), etc.; (6) detoxification variants of ADP-ribosylated toxins (e.g., Escherichia coli heat-labile toxin LT) and (7) other substances that act as immunostimulating agents to enhance the effectiveness of the composition. The present invention preferably uses the interferon inducer Poly (I: C).

The vaccine compositions including immunogenic compositions (e.g., may include the antigen, pharmaceutically acceptable carrier, and adjuvant), which typically will contain diluents, such as water, saline, glycerol, ethanol, etc. Additionally, auxiliary substances, such as wetting or emulsifying agents, pH buffering substances, and the like, may be present in such vehicles.

More specifically, vaccines comprising immunogenic compositions comprise an immunologically effective amount of the immunogenic polypeptides, as well as any other of the above-mentioned components, as needed. "immunologically effective amount" refers to the administration of that amount to an individual, either as part of a single dose or a continuous doseis effective for treatment or prevention. This amount varies depending upon the health and physical condition of the individual to be treated, the taxonomic group of individual to be treated (e.g., human), the capacity of the individual's immune system to synthesize antibodies, the degree of protection desired, the formulation of the vaccine, the treating doctor's assessment on the medical situation, and other relevant factors. It is expected that the amount will fall in a relatively broad range that can be determined through routine trials.

Typically, the vaccine compositions or immunogenic compositions are prepared as injectables, either as liquid solutions or suspensions; solid forms suitable for solution in, or suspension in, liquid excipient prior to injection may also be prepared. Theformulation also may be emulsified or encapsulated in liposomes for enhancing adjuvant effect.

In addition, the vaccine compositions of the present invention can be monovalent or multivalent vaccine.

The main advantages of the present invention include:

(1) The fusion protein of the present invention can induce a specific immune response against the oncoprotein of high-risk virus subtype HPV16 and HPV18 when used as a vaccine to achieve an efficient immune effect of an anticancer activity-related antigen.

(2) The fusion protein of the present invention is also capable of eliciting a specific immune response against other various HPV virus subtypes when used as vaccines to achieve a broad spectrum of immune effects against HPV.

(3) The HPV fusion protein of the present invention can stimulate the immune system to produce an immune response, including a humoral immune response and a cellular immune response.

(4) Immunization of animals using the HPV fusion protein of the present invention showed a significant tumor growth inhibition.

(5) The validation of the antigenic polypeptide sequence of the blood sample of the naturally infected HPV population demonstrates that the fusion protein of the present invention has good antigenicity in the human body.

(6) The sequence selection of each molecular target in the HPV fusion protein of the present invention reflects the greatest safety, reduces side effects or toxicity. The full length of the HPV oncoproteins E6, 7 have the functional activity for binding to the host DNA, and/or the Transcription factor. The introduction of the active protein into the human body has a greater risk, which may cause side effects or toxicity, and may lead to cell transformation resulting in the occurrence of the cancer. The antigenic sequence of the present invention has been subjected to an in-depth analysis of the structure and function of each HPV molecular target. The non-specific (homologous to non-high risk HPV subtypes) sequence was removed and the polypeptide sequence with transformed cell activity was removed.

The present invention will be further illustrated below with reference to the specific examples. It should be understood that these examples are only to illustrate the invention, not to limit the scope of the invention. The experimental methods with no specific conditions described in the following examples are generally performed under the conventional conditions (e.g., the conditions described by Sambrook et al., Molecular Cloning: A Laboratory Manual (New York: Cold Spring Harbor Laboratory Press, 1989)), or according to the manufacture's instructions. Unless indicated otherwise, parts and percentage are calculated by weight. The experimental materials and reagents used in the following examples are available from commercially available sources.

EXAMPLE 1

Construction of Fusion Protein Expression Plasmid

1. The gene sequence of HPV16 E7, E6, L2 gene sequence and gene sequence of HPV18 E7

Genebank No:

MT (SEQ ID NO. 1, derived from genebank Accession: P9WGU0.1)

HPV16-L2 (SEQ ID NO: 2, derived from Genebank Accession: AHK23261.1)

HPV16-E6 (SEQ ID NO: 3, derived from Genebank Accession: AHK23256.1)

HPV16-E7 (SEQ ID NO: 4, derived from Genebank Accession: AHK23257.1)

HPV18-E7 (SEQ ID NO: 5, derived from Genebank Accession: AGU 90424.1)

were optimized according to E. coli codon, and the optimized gene sequences were sent to GenScript Corporation (Nanjing) for synthesis. The product was identified and synthesized with a total length of 546bp of the encoding gene (atgggtgatcaggtgcattttcaaccgctgccgccggctgtggtcaaact-gtccgacgctctggatgaaatcgacggtc cggctggtcaggcagaaccg-gatgcgctcattacaacatcgtgaccttctgctgtaaatgcgattcaacgct-gcgtctg
tgtgtccagtcgacccacgtggatattcgcacgctggaagacctgct-gatgggcaccctgggtatcgttcagctgtacaa aacctgcaaacaagcaggcacgtgtccgccggatattatcccgaaagttctgagtgactc-
cgaagaagaaaacgatga
aattgacggtgtcaatcatcagcacctgccggcacgtcgcgcagaaccg-
caacgtcataccatgctgtgcatgtgctgt aaatgtgaagcccgcatcgaactg-
gtggttgaaagctctgeggatgacctgcgtgcctttcagcaactgttcctgaatac
gctgtetttcgtgtgcccgtggacgattcacgacatcatcctggaatgcgttcatcat-
catcaccatcac, SEQ ID NO.:13). The synthetic gene fragments were cloned into pET-28a plasmid (purchased from Sangon Biotech (Shanghai) Co., Ltd.) at the two restriction sites of Nco I/Hind III to construct pET-16L2E6E718E7 (hereinafter referred to as pET-VAC) vector.

The vector constructed with the gene sequence was pET-VAC-Pro. The constructed recombinant plasmid was identified by Nco I/Hind III digestion, and the results of DNA electrophoresis were shown in FIG. 1.

FIG. 1A shows the enzyme digestion results of the four pET-VAC-Pro clones, lane M was Maker, and lanes 1 to 4 were the result of the cleavage of pET-VAC-Pro clones 1 to 4, respectively. The results showed that only Clone pET-VAC-Pro-4 was digested to give a target band of about 550 bp (indicated by red arrows).

FIG. 1B shows the enzyme digestion electrophoretic results of the constructed pET-VAC plasmid, lane M was Maker, and lane 1 was the result of the electrophoresis of the pET-VAC plasmid, lane 1 was the result of the electrophoresis of the pET-VAC plasmid after digestion, and the red arrow indicated was the target band of about 550 bp.

Figure 2:
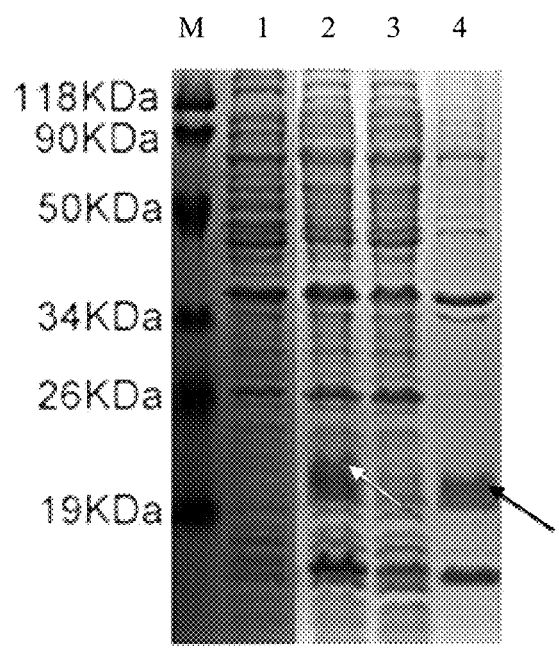
FIG. 2 shows the SDS-PAGE identification result of inducible expression of His-Vac recombinant protein.

2. Transformation of *E. coli* BL21 strain for inducing expression:

The recombinant plasmid pET-VAC vector was identified by restriction enzyme digestion and then transformed into BL21 strain by thermal shock for 42 s. BL21 was purchased from Shanghai Yingjun Biotechnology Co., Ltd. And positive strain was screened by Kan resistance. The results showed that the positive strains were induced for expression by IPTG in a final concentration of 0.1 mM. After the induction at 23° C. for 4 hours, the bacteria solution was taken for centrifugation, the SDS-PAGE identification results were shown in FIG. 2. The lane 1 was the uninduced whole bacteria and the lane 2 was the induced whole bacteria, lane 3 was the induced lysis supernatant, lane 4 was induced lysis sedimentation. In the figure, the red arrow indicated was the target protein His-Vac (fusion protein of the present invention) with a size of about 20 kDa.

3. Purification of the target protein by NI column

Figure 3:
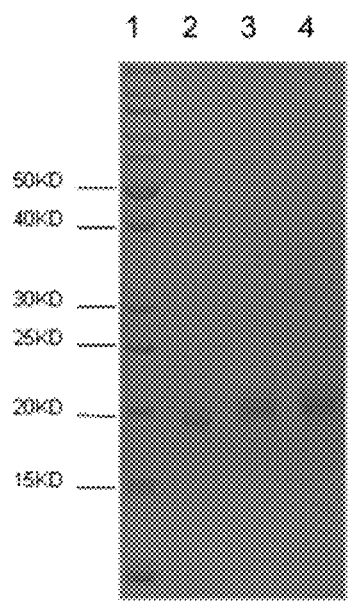
FIG. 3 shows the SDS-PAGE identification result of purified His-Vac recombinant protein.

Inclusion body was resolved with 8 M urea for PET-VAC recombinant protein, and purified by a Ni column (Ni-NTA; GE Healthcare), HiTrapQHP anion exchange chromatography. The protein purity was analyzed by SDS-PAGE. The results were showed in FIG. 3: the purity of the recombinant protein His-Vac protein was more than 95%. Lane 1 was Maker, lanes 2, 3, 4 were purified protein 5 μl, 10 μl, 15 μl for loading.

EXAMPLE 2

Mouse Immunization and Preparation of Immuno-antiserum

A total of 24 of C57BL/6 female mice, 8 weeks old, with about 20 grams of weight were purchased from Yangzhou University Experimental Animal Center. All of mice tails were cut and blood was collected for 100 μl before each immunization. Serum samples were centrifuged and stored at −20° C., ready for use. Twenty-four mice were randomly divided into 6 immunized dose groups and each group had 4 parallel control mice. Intraperitoneal injection of 100 μl in first immunization, and immunization dose were shown in Table 1. One week after the first immunization, mice tails were cut and blood was collected, and then subcutaneous injection of 5 points, a total injection of 100 μl. The dose was the same with that in the first immunization, as shown in Table 1. Blood was collected a week after the second immunization. The mice were sacrificed three weeks later and blood was sampled from eyes to detect the serum titer of mice immunized with cervical cancer vaccine.

TABLE 1

| | Immunization dose | | | | | |
|---|---|---|---|---|---|---|
| | No. | | | | | |
| | A | B | C | D | E | F |
| Dose (μg) | 0 | 10 | 50 | 100 | 150 | 200 |

EXAMPLE 3

ELISA Detection of Serum Titers after Immunization

Figure 4:
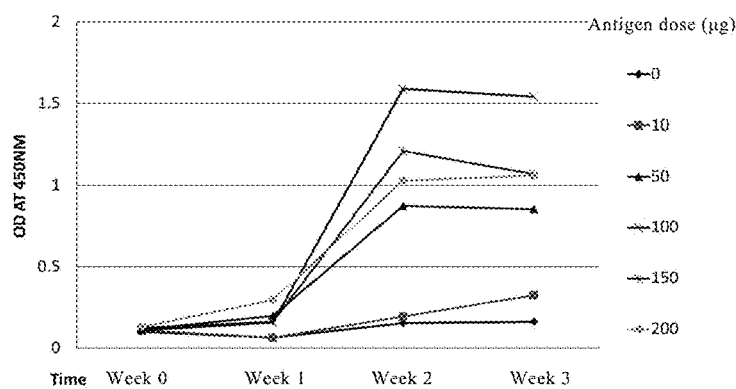
FIG. 4 shows the serum IgG ELISA results of mice after immunization with different doses, and IgG titers of mice serum of 1000-fold dilution.

1. Detection of serum IgG titers in mice after immunization with different doses His-Vac fusion protein was used as an antigen, 2 μg/ml and 100 μ/well for package and 4° C. overnight. Washed with PBST and dried, then 5% skim milk powder was added for blocking, 37° C. for 2 hours or 4° C. overnight. Washed with PBST and dried, and the mice serum of before immunization, immunization for one week, immunization for two weeks and immunization for three weeks were added. The serum was diluted with 1:1000, added 100 μl per well, and incubated at 37° C. for 1 h. Washed with PBST and dried, Goat anti-Mouse IgG (subclasses 1+2a+2b+3), Fcγ fragment specific, HRP (Cat: 115-035-164) diluted with 1:10000 purchased from Jackson were added. 37° C. incubation for 30 min, washed with PBST and dried, then TMB for color developing, terminated with 2 M $H_2SO_4$, reading OD value at 450 nm. The result was shown in FIG. 4, IgG is the main Ig in the body fluid, accounting for 70 to 75% of the total amount of Ig in the blood. After two immunizations, the IgG titer in the serum increased, and the serum titer of the mice began to rise between one week and two weeks after immunization. When the immunization dose was greater than 50 μg/mice, the titer of the second and third weeks after immunization reached the platform stage. When the His-Vac immunization dose was below 100 μg/mice, the IgG titer in the immune serum increased with the increase of His-Vac immunization dose, reaching the maximum at 100 μg/mice. And the titer of IgG in serum was decreased when the immunization dose was 150 μg/mice and 200 μg/mice.

Figure 5:
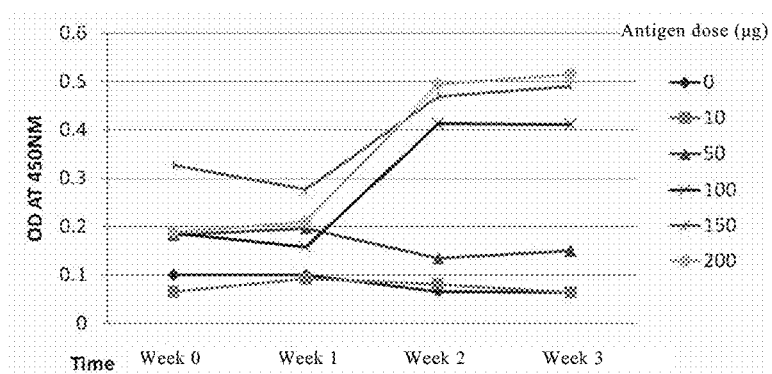
FIG. 5 shows the serum IgA ELISA results of mice after immunization with different doses, and IgA titers of mice serum of 1000-fold dilution.

2. Detection of serum IgA titers in mice after immunization with different doses His-Vac fusion protein was used as an antigen, 2 μg/ml and 100 μl/well for package and 4° C. overnight. Washed with PBST and dried, then 5% skim milk powder was added for blocking, 37° C. for 2 hours or 4° C. overnight. Washed with PBST and dried, and the mice serum of before immunization, immunization for one week, immunization for two weeks and immunization for three weeks were added. The serum was diluted with 1:1000, added 100 μl per well, and incubated at 37° C. for 1 h. Washed with PBST and dried, Goat anti-Mouse IgA in Mouse monoclonal antibody isotype reagents (Cat:ISO2-1KT) diluted with 1:10000 purchased from SIGMA were added. 37° C. incubation for 30 min, washed with PBST and dried, Rabbit Anti-Goat IgG (H+L)HRP(Cat:BS30503)diluted with 1:10000 purchased from Bioworld Technology were added. 37° C. incubation for 30 min, washed with PBST and dried, then TMB for color developing, terminated with 2 M $H_2SO_4$, reading OD value at 450 nm. The result was shown in FIG. 5, IgA content in serum is only lower than IgG, accounting for 10 to 20% of the serum immunoglobulin content. When the mouse immunization dose reached 100 μg/mice, the serum IgA titer in the mice began to rise between one week and two weeks after immunization and reached the platform in the third week. And when the immunization dose of mice was less than or equal to 50 μg/mice, IgA was substantially unchanged after immunization in mice, i.e. IgA antibody was not produced.

Figure 6:
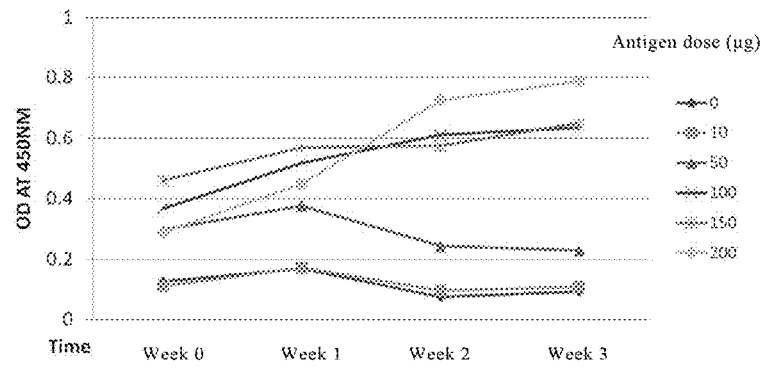
FIG. 6 shows the serum IgM ELISA results of mice after immunization with different doses, and IgM titers of mice serum of 1000-fold dilution.

3. Detection of serum IgM titers in mice after immunization with different doses His-Vac fusion protein was used as an antigen, 2 μg/ml and 100 μl/well for package and 4° C. overnight. Washed with PBST and dried, then 5% skim milk powder was added for blocking, 37° C. for 2 hours or 4° C. overnight. Washed with PBST and dried, and the mice serum of before immunization, immunization for one week, immunization for two weeks and immunization for three weeks were added. The serum was diluted with 1:1000, added 100 μl per well, and incubated at 37° C. for 1 h. Washed with PBST and dried, Goat anti-Mouse IgM in Mouse monoclonal antibody isotype reagents (Cat:ISO2-1KT) diluted with 1:10000 purchased from SIGMA were added. 37° C. incubation for 30min, washed with PBST and dried, Rabbit Anti-Goat IgG(H+L)HRP(Cat:BS30503)diluted with 1:10000 purchased from Bioworld Technology were added. 37° C. incubation for 30 min, washed with PBST and dried, then TMB for color developing, terminated with 2M $H_2SO_4$, reading OD value at 450 nm. The result was shown in FIG. 6, IgM antibodies were generally protective antibodies, which were antibodies that were secreted firstly in the immune response and were rapidly produced by infection. In the pre-immunized mouse serum, it may be due to the cross-linking effect of IgM so that the measured background value was somewhat higher. When the immunization dose reached 100 μg/mice, the IgM titer in the serum of the mice within one week after immunization began to rise and continued to rise untill the second week, and reached the platform in the third week. IgM was produced faster than IgG and IgA after vaccine immunization.

EXAMPLE 4

ELISA Determination of Serum Titer for Every Target in Serum after Immunization

Figure 7:
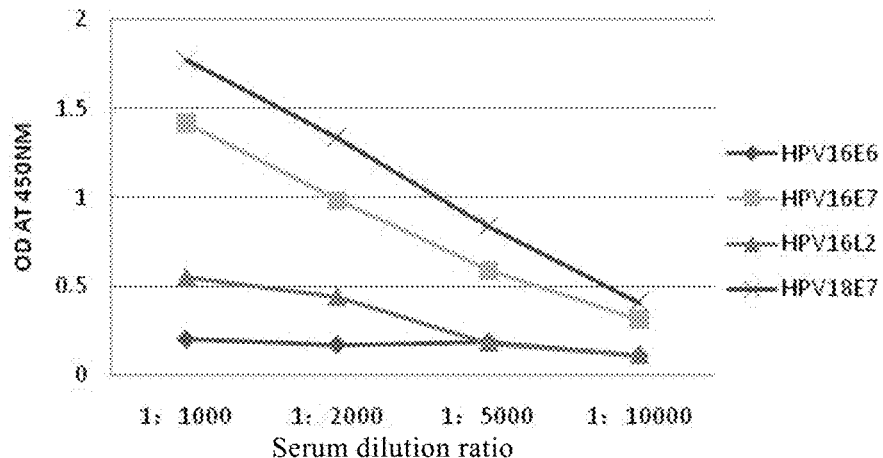
FIG. 7 shows the determination results of serum titer of mice serum against each protein molecule target after immunization with recombinant fusion protein antigen.

The cervical cancer vaccine His-Vac was fused with HPV16L2, HPV16E7, HPV18E7 and HPV16E6 each protein fragments. The binding of mouse serum to every target in His-Vac was detected after His-Vac immunization. The purified GST-HPV16E6, GST-HPV16E7, GST-HPV16L2 and GST-HPV18E7 were coated with 8 μg/ml and 100 μl/well, 4° C. overnight, washed with PBST and dried, then 5% skim milk powder was added for blocking, 37° C. for 2 hours or 4° C. overnight, washed with PBST and dried, then the serum of immune group D mice was added, with 1:1000, 1:2000, 1:5000, 1:10000 dilution, 100 μl per well, 37° C. incubation for 1 h. Washed with PBST and dried, Goat anti-Mouse IgG (subclasses 1+2a+2b+3), Fcγ fragment specific, HRP (Cat: 115-035-164) diluted with 1:10000 purchased from Jackson were added. 37° C. incubation for 30 min, washed with PBST and dried, then TMB for color developing, terminated with 2 M $H_2SO_4$, reading OD value at 450 nm. Results were shown in FIG. 7. The immunized mouse serum can stronglybe bound to HPV18E7, HPV16E7. Indicating that His-Vac immunized mice could stimulate the body to produce humoral immunity, and play an effective preventive effect.

EXAMPLE 5

Proliferation of Lymphocytes

Figure 8:
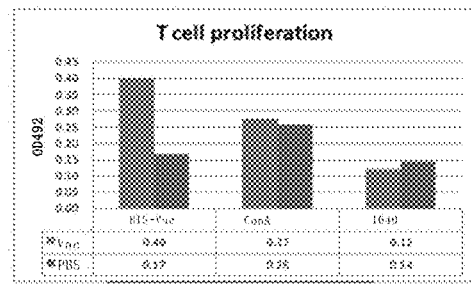
FIG. 8 shows the MTT assay results of His-Vac-induced lymphocyte proliferation.

The proliferation activity of His-Vac on lymphoid T cells was investigated with animal lymphocytes that were immunized with His-Vac protein and non-immunized animal lymphocytes (PBS in control group). Ten 10 of C57BL/6 mice were randomly divided into two groups, and each group had 5 parallel control mice. 100 μl of His-Vac (1 mg/ml) or PBS was intraperitoneally injected in the first immunization, and the immunization dose of His-Vac was 100 μg/mice. Two weeks after the first immunization, a total of 100 μl was injected by subcutaneous injection at 5 points, and the dose was the same with that in the first immunization. The third immunization was performed two weeks after the second immunization with the same dose as that in the second immunization. Mice were sacrificed one week after the third immunization. And the lymphocytes were isolated for cell proliferation experiments. 200 thousand lymphocytes were plated in each well of 96-well plate and incubated with no serum for 4 hours after adherence. His-Vac (50 μg/ml), concanavalin A (ConA) (5 μg/ml) and normal medium (1% FBS/1640) were diluted with 1% FBS/1640 and added 200 μl per well. And 72 h later, 20 μl of MTT was added and affected for four hours. The supernatant was washed and removed, and 150 μl of DMSO was added to each well, shaken on a decolorization shaker for 10 minutes and then measured at 492 nm. ConA could induce mice T cell's activation and proliferation, as a positive control. The results were shown in FIG. 8: the cell proliferation (OD value and cell picture) of lymphocytes isolated from His-Vac immunized mice was significantly observed when stimulated with His-Vac after adherent culture. However, there was no proliferation of the immunized lymphocytes unstimulated with His-Vac and the non-immunized lymphocytes stimulated with His-Vac.

EXAMPLE 6

C57BL/6 Mice Tumorigenesis Experiment

Figure 9:
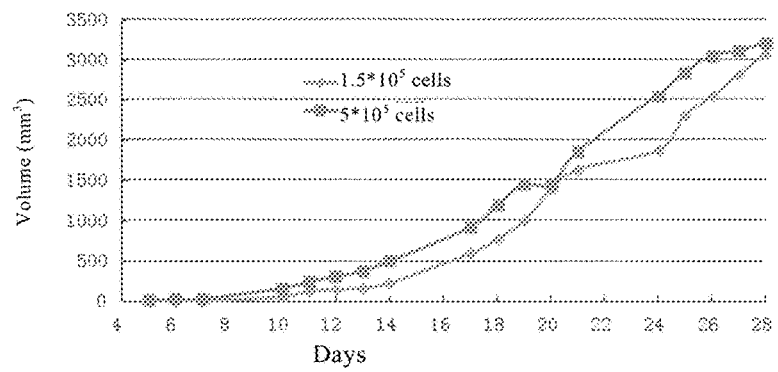
FIG. 9 shows the tumor model established by injecting the TC-1 cell to mice.

Four female C57BL/6 mice of 8 weeks were randomly divided into two groups. Tumor models were established in C57BL/6 mice with TC-1 tumor cells (i.e. C57BL/6 mice lung epithelial cells co-transformed with HPV16E6, E7 and ras genes), which was a cell model that studies high-risk subtypes of HPV16 virus activity and was commonly used in anti-HPV vaccine studies. Two mice were injected subcutaneously with $1.5 \times 10^5$ TC-1 cells in the left inguinal of the mice. Another two mice were injected subcutaneously with $5 \times 10^5$ TC-1 cells in the left inguinal of the mice, and the tumor size was measured daily. The tumor volume was calculated as volume=(length×width)/2. The results were shown in FIG. 9: when the number of TC-1 cells was $1.5 \times 10^5$, the initial tumor growth rate of mice was slower than $1.5 \times 10^5$, and the tumor was formed on about tenth day, and then the tumor increased rapidly, in line with the expected experimental requirements. Therefore, follow-up experiments used $1.5 \times 10^5$ for injection of tumors.

EXAMPLE 7

Experiments of His-Vac Inhibiting Mice Tumor

Figure 10A:
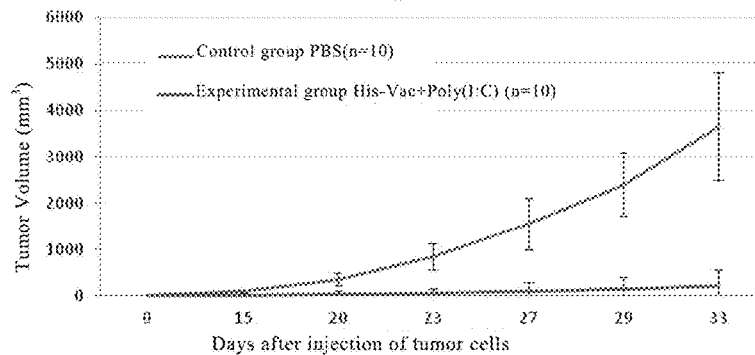
FIG. 10 shows the experimental results of inhibition for the tumor volume in mice by His-Vac; 10A shows the tumor inhibition test (His-Vac 3×100 µg; n=10), 10B shows the tumor volume of each mice alone in the tumor inhibition test.
Figure 10B:
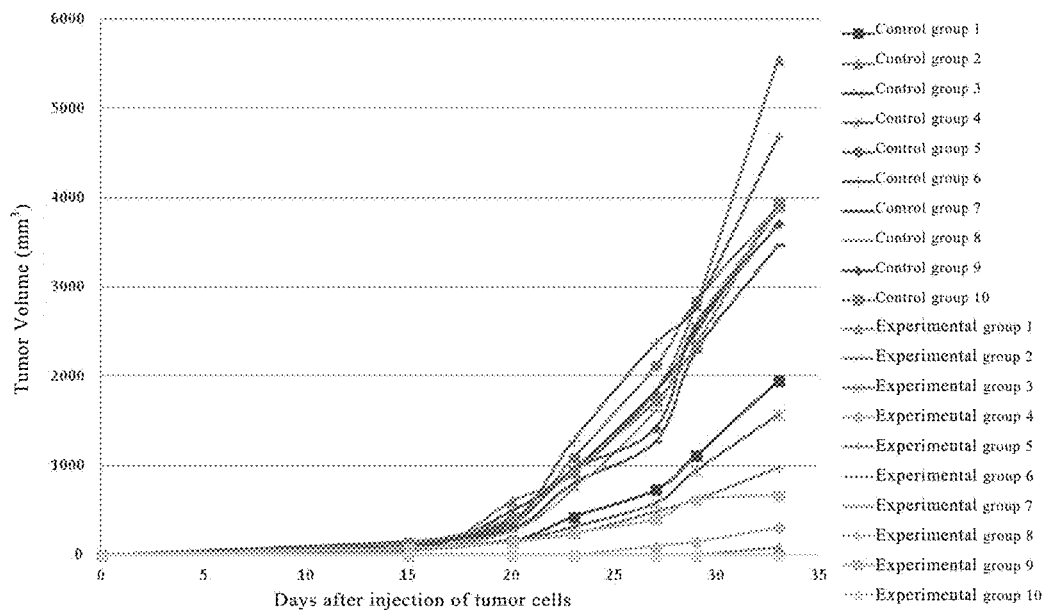
Figure 11A:
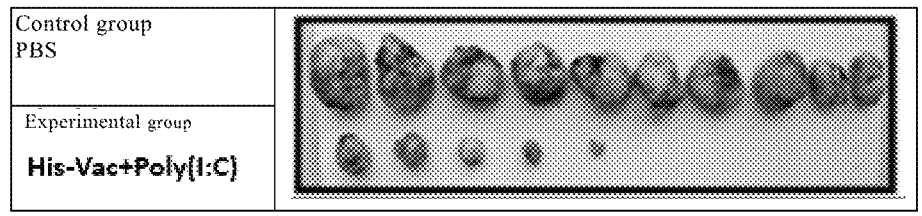
FIG. 11 shows the in vitro assay results for the inhibition of mice tumors by His-Vac; 11A is the in vitro comparison graph after removing the mice tumor; 11B is the weighing results of each mice tumor alone in the inhibition experiment; 11C is the average weight of the experimental group and control mice in inhibition experiment.
Figure 11B:
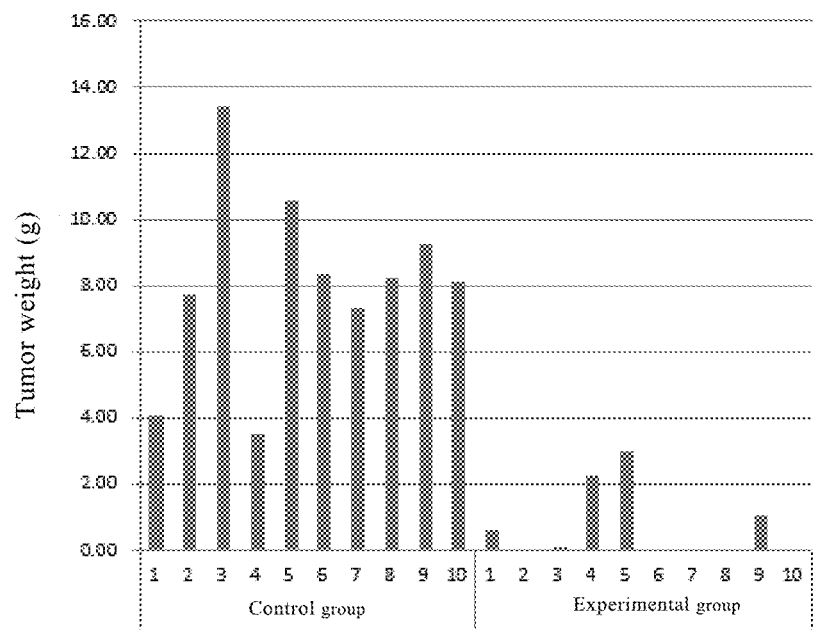
Figure 11C:
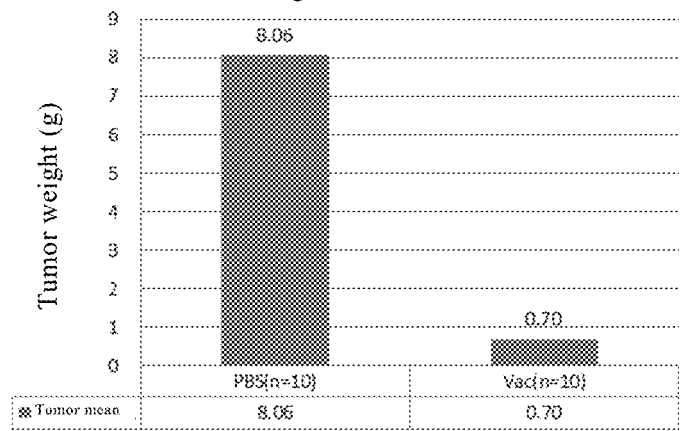

Mice TC-1 cell tumor model was used in in vivo antitumor activity experiments of vaccine protein. Immunization experiments were performed with 20 of C57BL/6 female mice with 8 weeks old and 20 grams, purchased from Yangzhou University Experimental Animal Center. The experimental and control groups each had 10 mice. The experimental group was immunized with 100 μg of His-Vac+50 μg Poly (I: C), while the control group used an equal volume of PBS. The complete Freund's adjuvant was used in the first immunization with intraperitoneal injection. The second immunization was performed 10 days after the first immunization using the incomplete Freund's adjuvant for back subcutaneous injection at multipoint. The third immunization was performed 2 weeks later, and immunization doses and manners were the same with that in the second immunization. The serum titer of the mice was measured by blood sampling after one week of the first immunization, and then the blood was collected once every other week. On the 14th day of the first immunization, the serum titer of mice reached the platform stage, and the TC-1 tumor cells were injected. Each mouse was injected with $1.5 \times 10^5$ cells into the left inguinal subcutaneous. 15 days after injection of tumor cells, tumor with a diameter of about 5 mm was formed. The size of the tumor was measuredtwice a week, and the data was collected to 33 days. Poly (I: C) was an interferon inducer and interferon was produced by the induction of the cell in vivo, having a similar role as interferon. Therefore, it had a broad-spectrum anti-virus and immune regulation function and could be used for adjuvant treatment of viral infectious diseases and tumors. In mice pre-immunized with His-Vac+Poly (I: C), tumor formation was significantly inhibited after injection of TC-1 cells, whereas mice injected with PBS were significantly tumorigenic. In FIG. 10, A was the average tumor volume measured at the time of survival of the experimental and control mice, and FIG. 10B was the volume of tumor formation per mouse alone. The mice in the experimental and control groups were immunized for 33 days for the first time on day 33 and sacrificed by taking blood from the eyeball. The tumor in mice were peeled off and weighed. The inhibition rate of His-Vac on tumor formation was calculated. The inhibition rate of tumor cell growth $$(\%) = \frac{\text{Average value } A \text{ of control group} - \text{Average value } A \text{ of experimentl group}}{\text{Average value } A \text{ of control group}} \times 100\%,$$

wherein the value A was the tumor weight. Results as shown in FIG. 11 (A, B, C), the inhibition rate of the tumor in the experimental group was 91%.

EXAMPLE 8

Experiments for Treating Mice Tumor Using His-Vac

Figure 12:
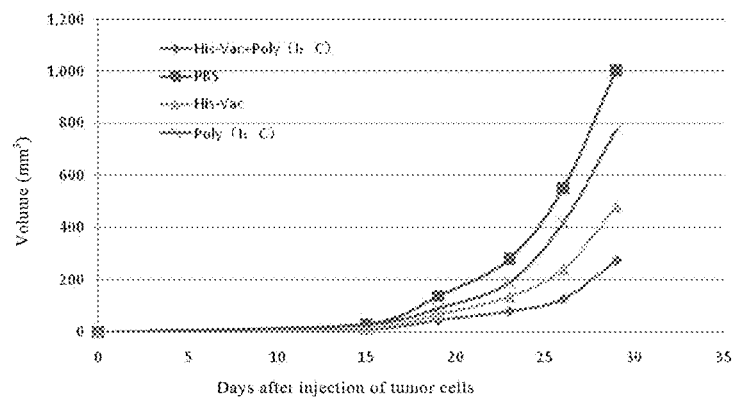
FIG. 12 shows the tumor burden results of tumor in mice treated with His-Vac for 30 days.

The protocol was that His-Vac vaccine was used for treatment after 7 days of TC-1 tumor cells injection. A total of 32 C57BL/6 female mice of 8 weeks old, having about 20 grams of weight, were purchased from Yangzhou University Experimental Animal Center. The mice were randomly divided into four groups: A, B, C and D, 8 mice for each group. Fresh TC-1 tumor cells in the logarithmic growth phase were subcutaneously injected into the left inguinal with $1.5 \times 10^5$ per mouse. Immunization was conducted 7 days after the injection. Complete Freund's adjuvant and emulsified protein were intraperitoneally injected in the first immunization. Group A was immunized with 100 μg of His-Vac+50 μg Poly (I: C); group B used an equal volume of PBS; group C was immunized with 100 μg of His-Vac; and group D used 50 μg Poly (I: C) and each mouse was injected with 100 μl. 7 days later, incomplete Freund's adjuvant and emulsified protein were subcutaneouslyinjected on multipoint in the second immunization and the amount of antigen usage was the same as that in the first immunization. 7 days later, the third immunization was conducted with the same immunization method and doses as that in the second immunization. On day 15, the tumor size was measured and measured every 3-4 days. The results were shown in FIG. 12: in group A, His-Vac combined with Poly (I: C) could significantly inhibit the growth rate of tumor, and the inhibition rate was 73%; in group C, His-Vac used alone also had a certain effect of tumor inhibition, and the inhibition rate was 52%, and its inhibition effect was weaker than that of His-Vac vaccine combined with Poly (I: C). While in group D, the Poly (I: C) used alone only had a tumor inhibition rate of 23%, indicating that His-Vac had a significant therapeutic effect on tumors in the growth process.

EXAMPLE 9

ELISA Detection for the Serum of HPV-infected and Unknown Population

Figure 13:
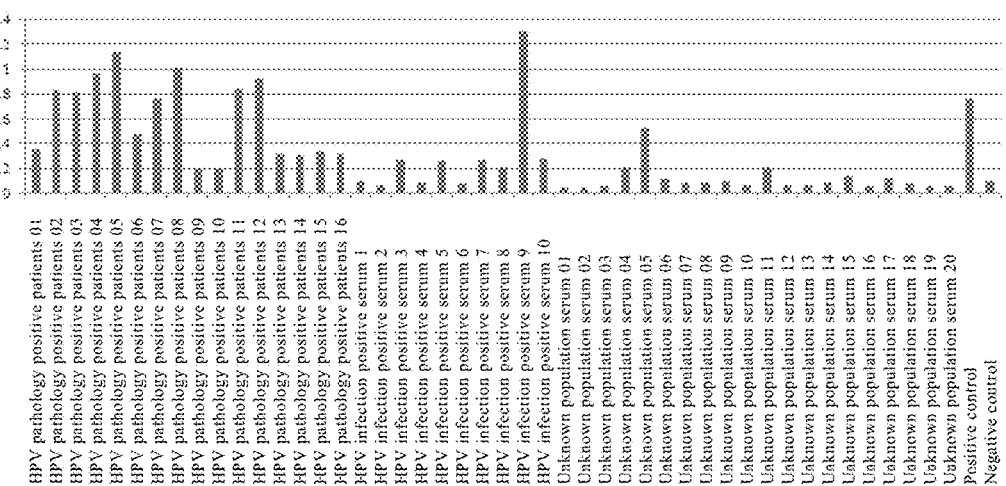
FIG. 13 shows the immunogenic results of His-Vac in human serum, the serum of positive pathology, positive infection and unknown populations is detected by ELISA.

Using indirect ELISA method: pET-VAC coated at 2 ug/ml was used to detect 16 cases of HPV positive serum of pathologically diagnosed cervical cancer, 10 cases of positive serum of HPV infection and 20 cases of serum of unknown population. Serum was diluted by 1:20, and adsorbed at 37° C. for 1 hour. The results were shown in FIG. 13: the detection of HPV positive serum of pathologically diagnosed cervical cancer were all positive (positive rate of 100%), the detection of the positive serum of HPV infection were positive in part (positive rate of 60%), the vast majority of the detection of unknown population was negative (positive rate was only 15%). Vaccine antigen pET-VAC test results showed that serum antibody response in three different populations could be significantly differentiated, indicating that the pET-VAC antigen of the present invention had good immunogenicity in the human body.

Discussion:

The His-Vac fusion protein provided by the invention has been proved having the dominant epitopes with strong immunological activity, through screening the serum of Chinese population and positive patients. The fusion protein could be used as a vaccine having the characteristics of strong antigenicity and high epitope specificity, and having the antigenic epitopes with broad spectrum activity, and which could neutralize many high-risk subtypes (L2).

The fusion protein of the invention could stimulate the humoral immunity in the animal, and had a strong neutralizing effect on the high-risk E7 protein. The binding of the L2 protein to the neutralizing antibody was weak and could weaken the inhibitory effect of the late protein antibody in serum on the vaccine protein.

The fusion protein could stimulate the proliferation of T cells in animals, and stimulate cell immunity. Therefore, the vaccine had a significant preventive effect on animal tumor formation, and combined with Poly (I: C) could significantly inhibit tumor formation. In addition, studies had shown that the vaccine had a good immunogenicity in the population and could be developed as preventative and/or therapeutic vaccines for HPV infection-related diseases (such as cervical cancer), and could also be used for HPV antibody detection.

Karanam B et al. (Vaccination with HPV16 L2E6E7 fusion protein in GPI-0100 adjuvant elicits protective humoral and cell-mediated immunity. Vaccine. 2009;27(7): 1040-9.) reported a HPV fusion protein (TA-CIN) composed of HPV16-type L2, E6 and E7 proteins in series, capable of inducing anti-HPV antibodies for the treatment of cervical cancer. But for infected people, antibodies against anti-late proteins were often present in the serum, which may have an inhibitory effect on the treatment of chimeric proteins. And the immunogenicity of the protein was low. The fusion protein of the present invention had a higher immunogenicity than TA-CIN, and serum IgG titer induced by the fusion protein of the present invention was 2.5 times of that of TA-CIN. And the fusion protein of the present invention had a significant advantage in inducing B cell and T cell proliferation and had shown better results in the treatment of HPV-related tumors. The construction of TA-CIN vaccine did not include HPV18 subtype antigen, and a large number of studies reported that HPV18 was the second most common carcinogenic high-risk subtype, second only to HPV16. Another potential risk of TA-CIN was the use of full-length of E6 and E7 oncoproteins as vaccine antigens. In recent years, a large number of studies had shown the relationship between the structure and function of E6, E7 oncoprotein and their molecular and cellular mechanisms of carcinogenic activity had been described. Because they had the activity of transforming cells and causing cancer, these two proteins could be served as therapeutic targets. The functional domain of E6, E7 binding to the host DNA and cytokine was still retained in the TA-CIN vaccine, so that the potential risk for immuned subject could not be ruled out when used as a vaccine.

In order to improve the safety of the vaccine, and to avoid the toxicity and the side effect, the invention has selected the sequence of the target antigen, removed the fragment having transformant activity in the E6 and E7 proteins, and retained the structural fragment having the dominant antigenicity in the human body.

All documents referred to in the present invention are incorporated by reference as if each reference is cited alone as a reference in the present application. In addition, it should be understood that after reading the teachings of the present invention described above, a skilled person in the art can make various changes or modifications of the invention, and these equivalent forms also fall into the scope as defined by the appended claims of the present application.

The invention claimed is:

1. A fusion protein, wherein the fusion protein comprises a first antigen element, a second antigen element, and optionally a tag sequence and/or a signal peptide sequence,
   wherein the first antigen element comprises a polypeptide derived from the Mycobacterium tuberculosis Psts-1 protein;
   the second antigen element comprises a polypeptide derived from a protein encoded by a HPV gene; and
   the second antigen element is one or more selected from the group consisting of an antigen element A, an antigen element B, an antigen element C, and an antigen element D,
   wherein the antigen element A is a polypeptide derived from HPV16 L2 protein, the antigen element B is a polypeptide derived from HPV16 E6 protein, the antigen element C is a polypeptide derived from HPV16 E7 protein, and the antigen element D is a polypeptide derived from the HPV18 E7 protein.

2. The fusion protein of claim 1, wherein the antigen element A comprises amino acids 17-36 of the HPV16 L2 protein; and/or
   the antigen element B comprises amino acids 29-38 of the HPV16 E6 protein; and/or
   the antigen element C comprises amino acids 36-90 of the HPV16 E7 protein; and/or
   the antigen element D comprises amino acids 31-100 of the HPV18 E7 protein.

3. The fusion protein of claim 1, wherein the fusion protein has the structure of formula I:

$$M\text{-}C\text{-}A\text{-}D\text{-}B\text{-}T \qquad (I),$$

wherein M is the first antigen element;
   A, B, C and D are the antigen element A, the antigen element B, the antigen element C, and the antigen element D, respectively;
   T is an optional tag sequence and/or a signal peptide sequence; and
   "-" means a peptide bond or a peptide linker linking the above-mentioned elements.

4. The fusion protein of claim 1, wherein the fusion protein is selected from the group consisting of:
   (A) a polypeptide having an amino acid sequence as shown in SEQ ID NO: 11 or 14;
   (B) a polypeptide having ≥80% identity to the amino acid sequence shown in SEQ ID NO: 11 or 14; and
   (C) a derivative polypeptide, which is derived from the amino acid sequence as shown in SEQ ID NO: 11 or SEQ ID NO: 14 by replacement, deletion, or addition of 1 to 5 amino acid residues.

5. The fusion protein of claim 1, wherein the fusion protein has one or more of the following properties:
   a) stimulating the body to produce a humoral immune response against HPV;
   b) stimulating the body to produce a cellular immune response against HPV;
   c) inducing T lymphocyte proliferation; and
   d) inducing HPV-specific CTL responses.

6. A pharmaceutical composition which comprises the fusion protein according to claim 1 and a pharmaceutically acceptable carrier and/or excipient.

7. A vaccine composition which comprises the fusion protein according to claim 1 and an immunologically acceptable carrier and/or excipient.

8. A method for treating HPV infection or HPV-related diseases comprising the steps of: administering the fusion protein according to claim 1 to a subject in need thereof.

9. The fusion protein of claim 1, wherein the length of the first antigen element is 15 to 30 amino acids; and/or
   the length of the antigen element A is 10 to 30 amino acids; and/or
   the length of the antigen element B is 5 to 20 amino acids; and/or
   the length of the antigen element C is 40 to 60 amino acids; and/or
   the length of the antigen element D is 50 to 100 amino acids.

10. The fusion protein of claim 1, wherein the second antigen element is:
    an antigen element A, an antigen element B, an antigen element C, and an antigen element D.

11. The fusion protein of claim 1, wherein the amino acid sequence of the Mycobacterium tuberculosis Psts-1 protein is shown in SEQ ID NO: 1.

12. The fusion protein of claim 1, wherein the amino acid sequence of the HPV16 L2 protein is shown in SEQ ID NO.: 2; and/or
    the amino acid sequence of the HPV16 E6 protein is shown in SEQ ID NO: 3; and/or
    the amino acid sequence of the HPV16 E7 protein is shown in SEQ ID NO: 4; and/or
    the amino acid sequence of the HPV18 E7 protein is shown in SEQ ID NO: 5.

13. The fusion protein of claim 4, wherein the fusion protein is a polypeptide having ≥90% identity to the amino acid sequence shown in SEQ ID NO: 11 or 14.

14. The fusion protein of claim 4, wherein the fusion protein is a polypeptide having ≥95% identity to the amino acid sequence shown in SEQ ID NO: 11 or 14.

15. The fusion protein of claim 4, wherein the fusion protein is a polypeptide having ≥97% identity to the amino acid sequence shown in SEQ ID NO: 11 or 14.

16. The fusion protein of claim 9, wherein the length of the first antigen element is 19 amino acids, and/or the length of the antigen element A is 20 amino acids, and/or the length of the antigen element B is 10 amino acids, and/or the length of the antigen element C is 55 amino acids, and/or the length of the antigen element D is 70 amino acids.

* * * * *

SEQUENCE LISTING

```
<160> NUMBER OF SEQ ID NOS: 14

<210> SEQ ID NO 1
<211> LENGTH: 374
<212> TYPE: PRT
<213> ORGANISM: Mycobacterium tuberculosis

<400> SEQUENCE: 1

Met Lys Ile Arg Leu His Thr Leu Leu Ala Val Leu Thr Ala Ala Pro
1               5                   10                  15

Leu Leu Leu Ala Ala Ala Gly Cys Gly Ser Lys Pro Pro Ser Gly Ser
            20                  25                  30

Pro Glu Thr Gly Ala Gly Ala Gly Thr Val Ala Thr Thr Pro Ala Ser
        35                  40                  45

Ser Pro Val Thr Leu Ala Glu Thr Gly Ser Thr Leu Leu Tyr Pro Leu
    50                  55                  60

Phe Asn Leu Trp Gly Pro Ala Phe His Glu Arg Tyr Pro Asn Val Thr
65                  70                  75                  80

Ile Thr Ala Gln Gly Thr Gly Ser Gly Ala Gly Ile Ala Gln Ala Ala
                85                  90                  95

Ala Gly Thr Val Asn Ile Gly Ala Ser Asp Ala Tyr Leu Ser Glu Gly
            100                 105                 110

Asp Met Ala Ala His Lys Gly Leu Met Asn Ile Ala Leu Ala Ile Ser
        115                 120                 125

Ala Gln Gln Val Asn Tyr Asn Leu Pro Gly Val Ser Glu His Leu Lys
    130                 135                 140
```

```
Leu Asn Gly Lys Val Leu Ala Ala Met Tyr Gln Gly Thr Ile Lys Thr
145                 150                 155                 160

Trp Asp Asp Pro Gln Ile Ala Ala Leu Asn Pro Gly Val Asn Leu Pro
                165                 170                 175

Gly Thr Ala Val Val Pro Leu His Arg Ser Asp Gly Ser Gly Asp Thr
            180                 185                 190

Phe Leu Phe Thr Gln Tyr Leu Ser Lys Gln Asp Pro Glu Gly Trp Gly
        195                 200                 205

Lys Ser Pro Gly Phe Gly Thr Thr Val Asp Phe Pro Ala Val Pro Gly
    210                 215                 220

Ala Leu Gly Glu Asn Gly Asn Gly Gly Met Val Thr Gly Cys Ala Glu
225                 230                 235                 240

Thr Pro Gly Cys Val Ala Tyr Ile Gly Ile Ser Phe Leu Asp Gln Ala
                245                 250                 255

Ser Gln Arg Gly Leu Gly Glu Ala Gln Leu Gly Asn Ser Ser Gly Asn
                260                 265                 270

Phe Leu Leu Pro Asp Ala Gln Ser Ile Gln Ala Ala Ala Gly Phe
        275                 280                 285

Ala Ser Lys Thr Pro Ala Asn Gln Ala Ile Ser Met Ile Asp Gly Pro
290                 295                 300

Ala Pro Asp Gly Tyr Pro Ile Ile Asn Tyr Glu Tyr Ala Ile Val Asn
305                 310                 315                 320

Asn Arg Gln Lys Asp Ala Ala Thr Ala Gln Thr Leu Gln Ala Phe Leu
                325                 330                 335

His Trp Ala Ile Thr Asp Gly Asn Lys Ala Ser Phe Leu Asp Gln Val
                340                 345                 350

His Phe Gln Pro Leu Pro Pro Ala Val Val Lys Leu Ser Asp Ala Leu
                355                 360                 365

Ile Ala Thr Ile Ser Ser
                370

<210> SEQ ID NO 2
<211> LENGTH: 473
<212> TYPE: PRT
<213> ORGANISM: human papilloma virus

<400> SEQUENCE: 2

Met Arg His Lys Arg Ser Ala Lys Arg Thr Lys Arg Ala Ser Ala Thr
1               5                   10                  15

Gln Leu Tyr Lys Thr Cys Lys Gln Ala Gly Thr Cys Pro Pro Asp Ile
                20                  25                  30

Ile Pro Lys Val Glu Gly Lys Thr Ile Ala Asp Gln Ile Leu Gln Tyr
                35                  40                  45

Gly Ser Met Gly Val Phe Phe Gly Gly Leu Gly Ile Gly Thr Gly Ser
            50                  55                  60

Gly Thr Gly Gly Arg Thr Gly Tyr Ile Pro Leu Gly Thr Arg Pro Pro
65              70                  75                  80

Thr Ala Thr Asp Thr Leu Ala Pro Val Arg Pro Pro Leu Thr Val Asp
                85                  90                  95

Pro Val Gly Pro Ser Asp Pro Ser Ile Val Ser Leu Val Glu Glu Thr
            100                 105                 110

Ser Phe Ile Asp Ala Gly Ala Pro Thr Ser Val Pro Ser Ile Pro Pro
        115                 120                 125

Asp Val Ser Gly Phe Ser Ile Thr Thr Ser Thr Asp Thr Thr Pro Ala
    130                 135                 140
```

```
Ile Leu Asp Ile Asn Asn Thr Val Thr Thr Val Thr His Asn Asn
145                 150                 155                 160

Pro Thr Phe Thr Asp Pro Ser Val Leu Gln Pro Pro Thr Pro Ala Glu
                165                 170                 175

Thr Gly Gly His Phe Thr Leu Ser Ser Ser Thr Ile Ser Thr His Asn
            180                 185                 190

Tyr Glu Glu Ile Pro Met Asp Thr Phe Ile Val Ser Thr Asn Pro Asn
        195                 200                 205

Thr Val Thr Ser Ser Thr Pro Ile Pro Gly Ser Arg Pro Val Ala Arg
    210                 215                 220

Leu Gly Leu Tyr Ser Arg Thr Thr Gln Gln Val Lys Val Val Asp Pro
225                 230                 235                 240

Ala Phe Val Thr Thr Pro Thr Lys Leu Ile Thr Tyr Asp Asn Pro Ala
                245                 250                 255

Tyr Glu Gly Ile Asp Val Asp Asn Thr Leu Tyr Phe Pro Asn Asn Asp
            260                 265                 270

Asn Ser Ile Asn Ile Ala Pro Asp Pro Asp Phe Leu Asp Ile Val Ala
        275                 280                 285

Leu His Arg Pro Ala Leu Thr Ser Arg Arg Thr Gly Ile Arg Tyr Ser
290                 295                 300

Arg Ile Gly Asn Lys Gln Thr Leu Arg Thr Arg Ser Gly Lys Ser Ile
305                 310                 315                 320

Gly Ala Lys Val His Tyr Tyr Asp Phe Ser Thr Ile Asp Pro Ala
                325                 330                 335

Glu Glu Ile Glu Leu Gln Thr Ile Thr Pro Ser Thr Tyr Thr Thr Thr
            340                 345                 350

Ser His Ala Ala Ser Pro Thr Ser Ile Asn Asn Gly Leu Tyr Asp Ile
        355                 360                 365

Tyr Ala Asp Asp Phe Ile Thr Asp Thr Phe Thr Pro Val Pro Ser
    370                 375                 380

Val Pro Ser Thr Ser Leu Ser Gly Tyr Ile Pro Ala Asn Thr Thr Ile
385                 390                 395                 400

Pro Phe Gly Gly Ala Tyr Asn Ile Pro Leu Val Ser Gly Pro Asp Ile
                405                 410                 415

Pro Ile Asn Ile Thr Asp Gln Ala Pro Ser Leu Leu Pro Ile Val Pro
            420                 425                 430

Gly Ser Pro Gln Tyr Thr Ile Ile Ala Asp Ala Gly Asp Phe Tyr Leu
        435                 440                 445

His Pro Ser Tyr Tyr Met Leu Arg Lys Arg Arg Lys Arg Leu Pro Tyr
    450                 455                 460

Phe Phe Ser Asp Val Ser Leu Ala Ala
465                 470

<210> SEQ ID NO 3
<211> LENGTH: 158
<212> TYPE: PRT
<213> ORGANISM: human papilloma virus

<400> SEQUENCE: 3

Met His Gln Lys Arg Thr Ala Met Phe Gln Asp Pro Gln Glu Arg Pro
1               5                   10                  15

Arg Lys Leu Pro His Leu Cys Thr Glu Leu Gln Thr Thr Ile His Asp
                20                  25                  30

Ile Ile Leu Glu Cys Val Tyr Cys Lys Gln Gln Leu Leu Arg Arg Glu
```

```
            35                  40                  45
Val Tyr Asp Phe Ala Phe Arg Asp Leu Cys Ile Val Tyr Arg Asp Gly
 50                  55                  60

Asn Pro Tyr Ala Val Cys Asp Lys Cys Leu Lys Phe Tyr Ser Lys Ile
 65                  70                  75                  80

Ser Glu Tyr Arg Tyr Tyr Cys Tyr Ser Val Tyr Gly Thr Thr Leu Glu
                 85                  90                  95

Gln Gln Tyr Asn Lys Pro Leu Cys Asp Leu Leu Ile Arg Cys Ile Asn
                100                 105                 110

Cys Gln Lys Pro Leu Cys Pro Glu Glu Lys Gln Arg His Leu Asp Lys
            115                 120                 125

Lys Gln Arg Phe His Asn Ile Arg Gly Arg Trp Thr Gly Arg Cys Met
        130                 135                 140

Ser Cys Cys Arg Ser Ser Arg Thr Arg Glu Thr Leu Leu
145                 150                 155

<210> SEQ ID NO 4
<211> LENGTH: 98
<212> TYPE: PRT
<213> ORGANISM: human papilloma virus

<400> SEQUENCE: 4

Met His Gly Asp Thr Pro Thr Leu His Glu Tyr Met Leu Asp Leu Gln
  1               5                  10                  15

Pro Glu Thr Thr Asp Leu Tyr Cys Tyr Glu Gln Leu Asn Asp Ser Ser
                 20                  25                  30

Glu Glu Glu Asp Glu Ile Asp Gly Pro Ala Gly Gln Ala Glu Pro Asp
             35                  40                  45

Arg Ala His Tyr Asn Ile Val Thr Phe Cys Cys Lys Cys Asp Ser Thr
 50                  55                  60

Leu Arg Leu Cys Val Gln Ser Thr His Val Asp Ile Arg Thr Leu Glu
 65                  70                  75                  80

Asp Leu Leu Met Gly Thr Leu Gly Ile Val Cys Pro Ile Cys Ser Gln
                 85                  90                  95

Lys Pro

<210> SEQ ID NO 5
<211> LENGTH: 100
<212> TYPE: PRT
<213> ORGANISM: human papilloma virus

<400> SEQUENCE: 5

Met His Gly Pro Lys Ala Thr Leu Gln Asp Ile Val Leu His Leu Glu
  1               5                  10                  15

Pro Gln Asn Glu Ile Pro Val Asp Leu Leu Cys His Glu Gln Leu Ser
                 20                  25                  30

Asp Ser Glu Glu Glu Asn Asp Glu Ile Asp Gly Val Asn His Gln His
             35                  40                  45

Leu Pro Ala Arg Arg Ala Glu Pro Gln Arg His Thr Met Leu Cys Met
 50                  55                  60

Cys Cys Lys Cys Glu Ala Arg Ile Glu Leu Val Val Glu Ser Ser Ala
 65                  70                  75                  80

Asp Asp Leu Arg Ala Phe Gln Gln Leu Phe Leu Asn Thr Leu Ser Phe
                 85                  90                  95

Val Cys Pro Trp
            100
```

<210> SEQ ID NO 6
<211> LENGTH: 19
<212> TYPE: PRT
<213> ORGANISM: Mycobacterium tuberculosis

<400> SEQUENCE: 6

Asp Gln Val His Phe Gln Pro Leu Pro Pro Ala Val Val Lys Leu Ser
1               5                   10                  15

Asp Ala Leu

<210> SEQ ID NO 7
<211> LENGTH: 20
<212> TYPE: PRT
<213> ORGANISM: human papilloma virus

<400> SEQUENCE: 7

Gln Leu Tyr Lys Thr Cys Lys Gln Ala Gly Thr Cys Pro Pro Asp Ile
1               5                   10                  15

Ile Pro Lys Val
            20

<210> SEQ ID NO 8
<211> LENGTH: 10
<212> TYPE: PRT
<213> ORGANISM: human papilloma virus

<400> SEQUENCE: 8

Thr Ile His Asp Ile Ile Leu Glu Cys Val
1               5                   10

<210> SEQ ID NO 9
<211> LENGTH: 55
<212> TYPE: PRT
<213> ORGANISM: human papilloma virus

<400> SEQUENCE: 9

Asp Glu Ile Asp Gly Pro Ala Gly Gln Ala Glu Pro Asp Arg Ala His
1               5                   10                  15

Tyr Asn Ile Val Thr Phe Cys Cys Lys Cys Asp Ser Thr Leu Arg Leu
                20                  25                  30

Cys Val Gln Ser Thr His Val Asp Ile Arg Thr Leu Glu Asp Leu Leu
            35                  40                  45

Met Gly Thr Leu Gly Ile Val
        50                  55

<210> SEQ ID NO 10
<211> LENGTH: 70
<212> TYPE: PRT
<213> ORGANISM: human papilloma virus

<400> SEQUENCE: 10

Leu Ser Asp Ser Glu Glu Glu Asn Asp Glu Ile Asp Gly Val Asn His
1               5                   10                  15

Gln His Leu Pro Ala Arg Arg Ala Glu Pro Gln Arg His Thr Met Leu
                20                  25                  30

Cys Met Cys Cys Lys Cys Glu Ala Arg Ile Glu Leu Val Val Glu Ser
            35                  40                  45

Ser Ala Asp Asp Leu Arg Ala Phe Gln Gln Leu Phe Leu Asn Thr Leu
        50                  55                  60

Ser Phe Val Cys Pro Trp
65                  70

<210> SEQ ID NO 11
<211> LENGTH: 174
<212> TYPE: PRT
<213> ORGANISM: Artificial sequence
<220> FEATURE:
<223> OTHER INFORMATION: fusion protein

<400> SEQUENCE: 11

Asp Gln Val His Phe Gln Pro Leu Pro Pro Ala Val Val Lys Leu Ser
1               5                   10                  15

Asp Ala Leu Asp Glu Ile Asp Gly Pro Ala Gly Gln Ala Glu Pro Asp
            20                  25                  30

Arg Ala His Tyr Asn Ile Val Thr Phe Cys Cys Lys Cys Asp Ser Thr
        35                  40                  45

Leu Arg Leu Cys Val Gln Ser Thr His Val Asp Ile Arg Thr Leu Glu
    50                  55                  60

Asp Leu Leu Met Gly Thr Leu Gly Ile Val Gln Leu Tyr Lys Thr Cys
65                  70                  75                  80

Lys Gln Ala Gly Thr Cys Pro Pro Asp Ile Ile Pro Lys Val Leu Ser
                85                  90                  95

Asp Ser Glu Glu Glu Asn Asp Glu Ile Asp Gly Val Asn His Gln His
            100                 105                 110

Leu Pro Ala Arg Arg Ala Glu Pro Gln Arg His Thr Met Leu Cys Met
        115                 120                 125

Cys Cys Lys Cys Glu Ala Arg Ile Glu Leu Val Val Glu Ser Ser Ala
    130                 135                 140

Asp Asp Leu Arg Ala Phe Gln Gln Leu Phe Leu Asn Thr Leu Ser Phe
145                 150                 155                 160

Val Cys Pro Trp Thr Ile His Asp Ile Ile Leu Glu Cys Val
                165                 170

<210> SEQ ID NO 12
<211> LENGTH: 546
<212> TYPE: DNA
<213> ORGANISM: Artificial sequence
<220> FEATURE:
<223> OTHER INFORMATION: nucleic acid sequence encoding the fusion
      protein

<400> SEQUENCE: 12
atgggcgacc aggttcactt ccagccgctg ccgccggctg ttgttaaact gtctgacgct      60
ctggatgaaa tagatggtcc agctggacaa gcagaaccgg acagagccca ttacaatatt     120 gtaaccttt gttgcaagtg tgactctacg cttcggttgt gcgtacaaag cacacacgta      180
gacattcgta cttttggaaga cctgttaatg ggcacactag gaattgtgca actttataaa    240
acatgcaaac aggcaggtac atgtccacct gacattatac ctaaggtttt aagcgactca    300
gaggaagaaa acgatgaaat agatggagtt aatcatcaac atttaccagc ccgacgagcc    360
gaaccacaac gtcacacaat gttgtgtatg tgttgtaagt gtgaagccag aattgagcta    420
gtagtagaaa gctcagcaga cgaccttcga gcattccagc agctgtttct gaacacactg    480
tcctttgtgt gtccgtggac tatacatgat ataatattag aatgtgtgca tcatcatcat    540
catcac                                                                546

<210> SEQ ID NO 13

```
<211> LENGTH: 546
<212> TYPE: DNA
<213> ORGANISM: Artificial sequence
<220> FEATURE:
<223> OTHER INFORMATION: nucleic acid sequence encoding the fusion
      protein

<400> SEQUENCE: 13
atgggtgatc aggtgcattt tcaaccgctg ccgccggctg tggtcaaact gtccgacgct     60
ctggatgaaa tcgacggtcc ggctggtcag gcagaaccgg atcgcgctca ttacaacatc    120
gtgaccttct gctgtaaatg cgattcaacg ctgcgtctgt gtgtccagtc gacccacgtg    180
gatattcgca cgctggaaga cctgctgatg ggcaccctgg gtatcgttca gctgtacaaa    240
acctgcaaac aagcaggcac gtgtccgccg gatattatcc cgaaagttct gagtgactcc    300
gaagaagaaa acgatgaaat tgacggtgtc aatcatcagc acctgccggc acgtcgcgca    360
gaaccgcaac gtcataccat gctgtgcatg tgctgtaaat gtgaagcccg catcgaactg    420
gtggttgaaa gctctgcgga tgacctgcgt gcctttcagc aactgttcct gaatacgctg    480
tctttcgtgt gcccgtggac gattcacgac atcatcctgg aatgcgttca tcatcatcac    540
catcac                                                              546

<210> SEQ ID NO 14
<211> LENGTH: 180
<212> TYPE: PRT
<213> ORGANISM: Artificial sequence
<220> FEATURE:
<223> OTHER INFORMATION: fusion protein

<400> SEQUENCE: 14

Asp Gln Val His Phe Gln Pro Leu Pro Pro Ala Val Val Lys Leu Ser
1               5                   10                  15

Asp Ala Leu Asp Glu Ile Asp Gly Pro Ala Gly Gln Ala Glu Pro Asp
            20                  25                  30

Arg Ala His Tyr Asn Ile Val Thr Phe Cys Cys Lys Cys Asp Ser Thr
        35                  40                  45

Leu Arg Leu Cys Val Gln Ser Thr His Val Asp Ile Arg Thr Leu Glu
    50                  55                  60

Asp Leu Leu Met Gly Thr Leu Gly Ile Val Gln Leu Tyr Lys Thr Cys
65                  70                  75                  80

Lys Gln Ala Gly Thr Cys Pro Pro Asp Ile Ile Pro Lys Val Leu Ser
                85                  90                  95

Asp Ser Glu Glu Glu Asn Asp Glu Ile Asp Gly Val Asn His Gln His
            100                 105                 110

Leu Pro Ala Arg Arg Ala Glu Pro Gln Arg His Thr Met Leu Cys Met
        115                 120                 125

Cys Cys Lys Cys Glu Ala Arg Ile Glu Leu Val Val Glu Ser Ser Ala
    130                 135                 140

Asp Asp Leu Arg Ala Phe Gln Gln Leu Phe Leu Asn Thr Leu Ser Phe
145                 150                 155                 160

Val Cys Pro Trp Thr Ile His Asp Ile Ile Leu Glu Cys Val His His
                165                 170                 175

His His His His
            180
```